(12) United States Patent
Carter et al.

(10) Patent No.: US 7,494,767 B2
(45) Date of Patent: Feb. 24, 2009

(54) ASSAY FOR TSG101 AS INHIBITORS OF HIV PRODUCTION

(75) Inventors: Carol Carter, Huntington, NY (US); Arthur Goff, Miller Place, NY (US); Lorna Ehrlich, Shoreham, NY (US); Stanley N. Cohen, Stanford, CA (US)

(73) Assignee: Functional Genetics, Inc., Gaithersburg, MD (US)

( * ) Notice: Subject to any disclaimer, the term of this patent is extended or adjusted under 35 U.S.C. 154(b) by 387 days.

(21) Appl. No.: 10/478,753

(22) PCT Filed: May 21, 2002

(86) PCT No.: PCT/US02/15965

§ 371 (c)(1),
(2), (4) Date: May 16, 2005

(87) PCT Pub. No.: WO02/094314

PCT Pub. Date: Nov. 28, 2002

(65) Prior Publication Data

US 2005/0287525 A1 Dec. 29, 2005

Related U.S. Application Data

(60) Provisional application No. 60/292,761, filed on May 21, 2001.

(51) Int. Cl.
C12Q 1/00 (2006.01)
C12Q 1/70 (2006.01)
C12Q 1/68 (2006.01)
G01N 33/53 (2006.01)

(52) U.S. Cl. ............... 435/4; 435/5; 435/6; 435/7.1

(58) Field of Classification Search ............ None
See application file for complete search history.

(56) References Cited

U.S. PATENT DOCUMENTS

| | | | |
|---|---|---|---|
| 5,344,774 A * | 9/1994 | Garry et al. | 435/239 |
| 6,093,405 A | 7/2000 | Zagury et al. | |
| 7,202,329 B2 * | 4/2007 | Wettstein et al. | 530/300 |
| 2002/0173622 A1 * | 11/2002 | Wettstein et al. | 530/350 |

FOREIGN PATENT DOCUMENTS

EP 1 033 401 A2 9/2000

OTHER PUBLICATIONS

Babst et al., "Mammalian Tumor Susceptibility Gene 101 (TSG101) and the Yeast Homologue, Vps23p, Both Function in Late Endosomal Trafficking.", *Traffic 2000*, vol. 1, pp. 248-258 (Mar. 2000).
Database GSP, "Human secreted protein, SEQ ID No. 5770", XP002331139, retrieved from EBI Database accession No. AAG01689 (Oct. 2000).
Dettenhofer et al., "Proline Residues in Human Immunodeficiency Virus Type 1 p6$^{Gag}$ Exert a Cell Type-Dependent Effect on Viral Replication and Virion Incorporation of Pol Proteins", *Journal of Virology*, vol. 73, No. 6, pp. 4696-4704 (Jun. 1999).
VerPlank et al., "Tsg101, a homologue of ubiquitin-conjugating (E2) enzymes, binds the L domain in HIV type 1 Pr55$^{Gag}$", *PNAS*, vol. 98, No. 14, pp. 7724-7729 (Jul. 2001).
Goff et al. "Tsg101 Control of Human Immunodeficiency Virus Type 1 Gag Trafficking and Release", *Journal of Virology*, vol. 77, No. 17, pp. 9173-9182 (Sep. 2003).

* cited by examiner

*Primary Examiner*—Bruce Campbell
*Assistant Examiner*—Louise Humphrey
(74) *Attorney, Agent, or Firm*—Jagtiani + Guttag

(57) ABSTRACT

The present invention provides methods for identifying peptides in a mammalian. Tsg101 protein that binds to the PTAPP (SEQ ID NO: 3) motif or L domain of human immunodeficiency virus type I (HIV-1). Such peptides can be used to inhibit Tsg101-HIV Gag binding, and is therefore effective in reducing HIV particle production. The invention also provides the peptides identified by the method of the invention and to method of using such peptides for treating HIV infection.

26 Claims, 9 Drawing Sheets

A. Pr55^Gag

B. p1-p6

Figure 1A:
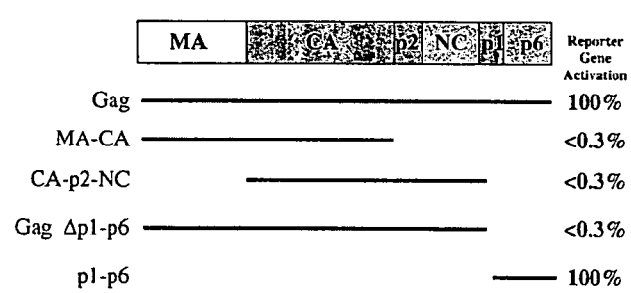

A.

GagΔp6 − − +
Gag − + −

68—
　　　　— Gag
43— 　— GagΔp6

20—

18— — NC-p6
14— — NC 1 2 3

Western: Anti-NC

B.

IP : anti-Tsg101₁

GagΔp6 − − +　　GagΔp6 − − +
Gag − + −　　　Gag − + −

68—　　　　　　　68—
— Gag
43—　　　　　　　43— — — — Tsg101

20—　　　　　　　20—

18— — NC-p6　　18—
14—　　　　　　　14—

1 2 3　　　　　4 5 6

Western: Anti-NC　　　Anti-Tsg101₂

C.

IP : anti-CA　　　IP : anti-CA

Gag − +　　　　Gag − +

68—　　　　　　　68—
43— — Tsg101　43— — Gag
　　　　　　　　　　— MA-CA
20—　　　　　　　20—
　　　　　　　　　　— CA
18—　　　　　　　18—

1 2　　　　　　3 4

Western: Anti-Tsg101₁　　Anti-CA

FIGS. 3A-3C

A.

B.

SEQUENCE LISTING

<160> NUMBER OF SEQ ID NOS: 49

<210> SEQ ID NO 1
<211> LENGTH: 391
<212> TYPE: PRT
<213> ORGANISM: Mus sp.

<400> SEQUENCE: 1

Met Ala Val Ser Glu Ser Gln Leu Lys Lys Met Met Ser Lys Tyr Lys
 1               5                  10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser

```
                    35                  40                  45
Ser Arg Glu Leu Val Asn Leu Thr Gly Thr Ile Pro Val Arg Tyr Arg
         50                  55                  60

Gly Asn Ile Tyr Asn Ile Pro Ile Cys Leu Trp Leu Leu Asp Thr Tyr
 65                  70                  75                  80

Pro Tyr Asn Pro Pro Ile Cys Phe Val Lys Pro Thr Ser Ser Met Thr
                 85                  90                  95

Ile Lys Thr Gly Lys His Val Asp Ala Asn Gly Lys Ile Tyr Leu Pro
             100                 105                 110

Tyr Leu His Asp Trp Lys His Pro Arg Ser Glu Leu Leu Glu Leu Ile
         115                 120                 125

Gln Ile Met Ile Val Ile Phe Gly Glu Glu Pro Pro Val Phe Ser Arg
     130                 135                 140

Pro Thr Val Ser Ala Ser Tyr Pro Pro Tyr Thr Ala Thr Gly Pro Pro
145                 150                 155                 160

Asn Thr Ser Tyr Met Pro Gly Met Pro Ser Gly Ile Ser Ala Tyr Pro
                165                 170                 175

Ser Gly Tyr Pro Pro Asn Pro Ser Gly Tyr Pro Gly Cys Pro Tyr Pro
             180                 185                 190

Pro Ala Gly Pro Tyr Pro Ala Thr Thr Ser Ser Gln Tyr Pro Ser Gln
         195                 200                 205

Pro Pro Val Thr Thr Val Gly Pro Ser Arg Asp Gly Thr Ile Ser Glu
     210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
                245                 250                 255

Leu Lys Arg Thr Glu Glu Asp Leu Lys Lys Gly His Gln Lys Leu Glu
             260                 265                 270

Glu Met Val Thr Arg Leu Asp Gln Glu Val Ala Glu Val Asp Lys Asn
         275                 280                 285

Ile Glu Leu Leu Lys Lys Lys Asp Glu Glu Leu Ser Ser Ala Leu Glu
     290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
             340                 345                 350

Gly Val Ile Asp Leu Asp Val Phe Leu Lys His Val Arg Leu Leu Ser
         355                 360                 365

Arg Lys Gln Phe Gln Leu Arg Ala Leu Met Gln Lys Ala Arg Lys Thr
     370                 375                 380

Ala Gly Leu Ser Asp Leu Tyr
385                 390

<210> SEQ ID NO 2
<211> LENGTH: 390
<212> TYPE: PRT
<213> ORGANISM: Homo sapiens

<400> SEQUENCE: 2

Met Ala Val Ser Glu Ser Gln Leu Lys Lys Met Val Ser Lys Tyr Lys
 1               5                  10                  15
```

```
Tyr Arg Asp Leu Thr Val Arg Glu Thr Val Asn Val Ile Thr Leu Tyr
            20                  25                  30

Lys Asp Leu Lys Pro Val Leu Asp Ser Tyr Val Phe Asn Asp Gly Ser
        35                  40                  45

Ser Arg Glu Leu Met Asn Leu Thr Gly Thr Ile Pro Val Pro Tyr Arg
    50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
                100                 105                 110

Tyr Leu His Glu Trp Lys His Pro Gln Ser Asp Leu Leu Gly Leu Ile
            115                 120                 125

Gln Val Met Ile Val Val Phe Gly Asp Glu Pro Pro Val Phe Ser Arg
130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
                180                 185                 190

Gly Gly Pro Tyr Pro Ala Thr Thr Ser Ser Gln Tyr Pro Ser Gln Pro
            195                 200                 205

Pro Val Thr Thr Val Gly Pro Ser Arg Asp Gly Thr Ile Ser Glu Asp
        210                 215                 220

Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
                260                 265                 270

Met Val Thr Arg Leu Asp Gln Glu Val Ala Glu Val Asp Lys Asn Ile
            275                 280                 285

Glu Leu Leu Lys Lys Lys Asp Glu Glu Leu Ser Ser Ala Leu Glu Lys
        290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
                340                 345                 350

Val Ile Asp Leu Asp Val Phe Leu Lys His Val Arg Leu Leu Ser Arg
            355                 360                 365

Lys Gln Phe Gln Leu Arg Ala Leu Met Gln Lys Ala Arg Lys Thr Ala
        370                 375                 380

Gly Leu Ser Asp Leu Tyr
385                 390

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued

```
                peptide

<400> SEQUENCE: 3

Pro Thr Ala Pro Pro
 1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Gln Ser Arg Pro Glu Pro Thr Ala Pro Pro Glu Glu Ser
 1               5                  10                  15

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggctagaagg atccggatgg gtgcgagagc gtcag                              35

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaagatctat tagaagttta aagtgc                                        26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaagatctca ctacaaaact cttgcc                                        26

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggaagatctc ccctatagtg cagaacatcc                                    30

<210> SEQ ID NO 9
<211> LENGTH: 23
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 9
cgggatcctt ccctggcctt ccc                                          23

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggaagatct ggccttcc                                                18

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaagatctat tagaagttta aagtgc                                       26

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagagcagac cagagtttct tcagagcaga cc                                32

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cagagcagac cagaggaaga gagcttcagg                                   30

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cccctcagag ccaggagcc                                               19

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
gccgatagac agggaactgt atc                                              23

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccgatagaca aggaaaacga cccctcgtca c                                     31

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
catttcctat atgtagtata tag                                              23

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gaccagaggc aacagcc                                                     17

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagagccaac agccgcagca tttcttcaga gc                                    32

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaattcatgg cggtgtcgga gagc                                             24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 21
gtcgactcag tagaggtcac tgag                                          24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtcgactcat gcctggtatg gcgg                                          24

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtcgactcag ggaccaacag tggtcac                                       27

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtcgactcag ttttcagact gattttcc                                      28

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gaattccctc cagtcttctc tcgtcc                                        26

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gaattccgga tgaaggagga aatggatcg                                     29

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 27
gaattcaatg atatcgatga agttatcatt ccc                                33

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gttgatgcaa atggggcgat atatcttcc                                     29

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aatgggaaga tatggcttcc ttatctac                                      28

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gggaagatat atcttcctgc tctacatgaa tgg                                33

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ccttatctac atgaagcgaa acacccacag                                    30

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctacatgaat gggcacaccc acagtcag                                      28

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
```

-continued ggatccatgg tgtccaagta c                                              21

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggatcctcag tagaggtcac tgag                                           24

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggaagatctg gccttcctac aagggaaggc cagggaatt                           39

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccatgtattg atagataact atgtctg                                        27

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaagatctg gccttcctac aagggaaggc cagggaatt                           39

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccatgtattg atagataact atgtctg                                        27

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Pro Thr Ala Pro
  1

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 40

His His His His His His
  1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid

<400> SEQUENCE: 41

Leu Xaa Xaa Leu Xaa Xaa Leu Xaa Xaa Leu Xaa Xaa
  1               5                  10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thr or Ser

<400> SEQUENCE: 42

Pro Xaa Ala Pro Pro
  1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Ile Ala Pro Pro
  1               5
```

```
<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: May or may not be present

<400> SEQUENCE: 44

Pro Pro Pro Pro Tyr
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Thr Ala Pro Pro
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Thr Ala Ala Ala
 1               5

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Asn Gly Asn Ile Cys Leu Asp Ile Leu Lys Asp Gln Trp Ser
 1               5                  10                  15

<210> SEQ ID NO 48
<211> LENGTH: 14
<212> TYPE: PRT
<213> ORGANISM: Homo sapiens

<400> SEQUENCE: 48

Ala Asn Gly Lys Ile Tyr Leu Pro Tyr Leu His Glu Trp Lys
 1               5                  10

<210> SEQ ID NO 49
<211> LENGTH: 14
```

-continued

```
<212> TYPE: PRT
<213> ORGANISM: Mus sp.

<400> SEQUENCE: 49

Ala Asn Gly Lys Ile Tyr Leu Pro Tyr Leu His Asp Trp Lys
 1               5                  10
```

US 7,494,767 B2

ASSAY FOR TSG101 AS INHIBITORS OF HIV PRODUCTION

This application claims the benefit, under 35 U.S.C. §119 (e), of U.S. Provisional Patent Application No. 60/292,761, filed on May 21, 2001, which is incorporated herein by reference in its entirety.

This invention was made with U.S. Government support. Accordingly, the U.S. Government has certain rights in the invention.

1. FIELD OF THE INVENTION

The present invention relates to methods for identifying peptides in a mammalian Tsg101 protein, which is effective in reducing retroviral particle production, e.g., HIV particle production. The invention also relates to the peptides identified by the method of the invention and to method of using such peptides for treating retroviral infection, HIV infection.

2. BACKGROUND OF THE INVENTION

The Pr55$^{Gag}$ protein of the human immunodeficiency virus type I (HIV-1) contains all of the information required for transport to assembly sites on the plasma membrane, association with genomic RNA, and release into extracellular space (see, e.g., Swanstrom, R. & Wills, J. W., 1997, in Retroviruses, eds. Coffin, J. M., Hughes, S. H. & Varmus, H. E., Cold Spring Harbor Laboratory Press, New York, pp. 263-334). However, although Gag is sufficient for viral assembly, cellular proteins are likely to facilitate the process. Several cellular proteins can be recovered from purified virions, suggesting proximity to the assembling particle (see, e.g., Arthur, L. O., Bess, J. W., Jr., Sowder, R. C. I., Benveniste, R. E., Mann, D. L., Chermann, J.-C. & Henderson, L. E., 1992, Science 258, 1935-1938; and Ott, D. E., Coren, L. V., Kane, B. P., Busch, L. K., Johnson, D. J. Sowder, R. C. I., Chertova, E. N., Arthur, L. O. & Henderson, L. E., 1996, J Virol. 70, 7734-7743). Others interact directly with Pr55$^{Gas}$ (see, e.g., Luban, B., Bossolt, K. L., Franke, E. K., Kalpana, G. V. & Goff, S. P., 1993, Cell 73, 1067-1078). Interaction with still others is implied, since Gag contains post-translational modifications (see, e.g., Bryant, M. & Ratner, L., 1990, Proc. Natl. Acad. Sci. USA 87, 523-527; Camaur, D., Gallay, P., Swingler, S. & Trono, D., 1997, J. Virol. 71,6834-6841; Göttlinger, H. G., Sodroski, J. G. & Haseltine, W. A., 1989, Proc. Natl. Acad. Sci. USA 86,5781-5785; Ott, D. E., Coren, L. V., Copeland, T. D., Kane, B. P., Johnson, D. G., Sowder, R. C., 2nd, Yoshinaka, Y., Oroszlan, S., Arthur, L. O. & Henderson, L. E., 1998, J. Virol. 72, 2962-2968). There are now reports that the region in Gag required for release of mature particles, the late (L) domain (see, e.g., Wills, J. W., Cameron, C. E., Wilson, C. B., Xiang, Y., Bennett, R. P. & Leis, J., 1994, J. Virol. 68, 6605-6618; Göttlinger, H. G., Dorfman, T., Sodroski, J. G. & Haseltine, W. A., 1991, Proc. Natl. Acad Sci. USA 88, 3195-3199; Huang, M., Orenstein, J. M., Martin, M. A. & Freed, E. O., 1995, J. Virol. 69, 6810-6818) directs the interaction of the protein with the ubiquitination machinery (see, e.g., Schubert, U., Ott, D. E., Chertova, E. N., Welker, R., Tessmer, U., Princiotta, M. F., Bennink, J. R., Krausslich, H. G. & Yewdell, J. W., 2000, Proc. Natl. Acad. Sci. USA 97, 13057-13062; Strack, B., Calistri, A., Accola, M. A., Palu, G. & Gottlinger, H. G., 2000, Proc. Natl. Acad. Sci. USA 97, 13063-13068; Vogt, V. M., 2000, Proc. Natl. Acad Sci. USA 97, 12945-12947; Ott, D. E., Coren, L. V., Chertova, E. N., Gagliardi, T. D. & Schubert, U., 2000, Virology 278, 111-121, Patnaik, A., Chau, V. & Wills, 3. W., 2000, Proc. Natl. Acad Sci. USA 97, 13069-13074). Based on its sequence and recent studies, Tsg101 is an ubiquitin (Ub)-conjugating E2 enzyme variant (UEV) protein involved in regulation of intracellular trafficking, transcriptional regulation, and cell cycle control (see, e.g., Babst, M., Odorizzi, G., Estepa, E. J. & Emr, S. D., 2000, Traffic 1,242-258; Lemmon, S. K. & Traub, L. M., 2000, Curr. Opin Cell Biol. 12,457-466, Xie, W., Li, L. & Cohen, S. N., 1998, Proc. Natl. Acad. Sci. USA 95, 1595-1600; Zhong, Q., Chen, Y., Jones, D. & Lee, W. H., 1998, Cancer Res. 58,2699-2702; Sun, Z., Pan, 3., Hope, W. X., Cohen, S. N. & Balk, S. P., 1999, Cancer 86,689- 96). UEV proteins lack the critical Cys residue essential for conjugation and transfer of Ub to protein substrates or Ub-ligating (E3) enzymes (Koonin, E. V. & Abagyan, R. A., 1997, Nat. Genet. 16,330-331; Ponting, C. P., Cai, Y.-D. & Bork, P., 1997, J. Mol. Med. 75,467-469). They are highly conserved in evolution and constitute a novel family of proteins structurally related to, but distinct from, E2 enzymes.

All retroviruses have in common 3 genes, gag, pol, and env, which specify the structural and enzymatic functions of the virus (see, e.g., Swanstrom, R. & Wills, J. W., 1997, in Retroviruses, eds. Coffin, J. M., Hughes, S. H. & Varmus, H. E., Cold Spring Harbor Laboratory Press, New York, pp. 263-334). The gag gene alone is sufficient for assembly and release of immature virus-like particles from infected cells. Maturation to form the infectious particle requires a viral-encoded protease (PR) encoded in pol. The gag-encoded protein (Gag) contains distinct domains involved in assembly and release. There is a plasma membrane-binding (M) domain located in the N-terminal matrix (MA) region, a capsid (CA) domain that forms a genome-encasing core structure, a protein interaction (I) domain in the nucleocapsid (NC) region, and a late (L) domain, required for release by budding from the plasma membrane. The L domain is a Pro-rich motif that is highly conserved in retroviruses; other enveloped viruses, including rhabdo-, fib-, and Epstein Barr viruses, and cellular proteins also have Pro-rich motifs (Harty, R. N., Brown, M. E., Wang, G., Huibregtse, I. & Hayes, F. P., 2000, Proc. Natl. Acad Sd. USA 97, 13871-13876; Wills, J. W., Cameron, C. E., Wilson, C. B., Xiang, Y., Bennett, R. P. & Leis, J., 1994, J Virol. 68, 6605-6618; Göttlinger, H. G., Dorfman, T., Sodroski, J. G. & Haseltine, W. A., 1991, Proc. Natl. Acad Sci. USA 88, 3195-3199; Huang, M., Orenstein, J. M., Martin, M. A. & Freed, E. O., 1995, J. Virol. 69, 6810-6818; Ikeda, M., Ikeda, A., Longan, L. C. & Longnecker, R., 2000, Virol. 268, 178-191; Yasuda, J. & Hunter, E., 1998, J. Virol. 72, 4095-4103; Harty, R. N., Paragas, J., Sudol, M. & Palese, P., 1999, J. Virol. 73, 2921-2929). The L domains in retroviruses differ in amino acid sequence and location within the respective viral structural proteins, but are functionally exchangeable (Wills, J. W., Cameron, C. E., Wilson, C. B., Xiang, Y., Bennett, R. P. & Leis, J., 1994, J. Virol. 68, 6605-6618; Parent, L. J., Bennett, R P., Craven, R. C., Nelle, T. D., Krishna, N. K., Bowzard, J. B., Wilson, C. B., Puffer, B. A., Montelaro, R. C. & Wills, J. W., 1995, J. Virol. 69, 5455-5460), suggesting commonality of function.

The protein product of the TSG101 gene was originally identified by the reversible neoplasia associated with its functional inactivation in murine fibroblasts (Li, L. & Cohen, S. N., 1996, Cell 85, 319-329). Sequence analysis has suggested (Li, L. & Cohen, S. N., 1996, Cell 85, 319-329; Koonin, E. V. & Abagyan, R. A., 1997, Nat. Genet. 16,330-331; Ponting, C. P., Cai, Y.-D. & Bork, P., 1997, J. Mol. Med. 75, 467-469), and experimental evidence has shown, that Tsg101 can function in both the modulation of transcription (Sun, Z., Pan, J., Hope, W. X., Cohen, S. N. & Balk, S. P., 1999, Cancer 86, 689-96; Watanabe, M., Yanagi, Y., Masahiro, Y., Yano, T., Yoshikawa, H., Yanagisawa, J., & Kato, S., 1998, *Biochem, Biophys. Res. Commun.* 245, 900-905; Hittleman, A. B., Burakov, D., Iniguez-Lluhi, J. A., Freedman, L. P., & Garabedian, M. J., 1999, *EMBO* 3, 18, 5380-5388) and the inhibition of ubiquitination and protein decay (Li, L., Liao, J., Ruland, J., Mak, T. W., & Cohen, C. N., 2001, *Proc. Natl. Acad. Sci. USA* 98, 1619-1624). The latter effects are mediated by an N-terminal region that contains a ubiquitin (Ub) conjugase (E2)-like domain, but lacks an active site Cys residue crucial to Ub conjugation. The structure of the UEV domain of Tsg101 and its modes of interaction with Ub and PTAP (SEQ ID NO: 39) have also been reported (Pornillos et al., 2002, *EMBO J.* 21:2397-2406).

Cells deficient in Tsg101 show a variety of nuclear, microtubule, and mitotic spindle abnormalities (Xie, W., Li, L. & Cohen, S. N., 1998, *Proc. Natl. Acad. Sci. USA* 95, 1595-1600; Zhong, Q., Chen, Y., Jones, D. & Lee, W. H., 1998, *Cancer Res.* 58, 2699-2702), and tsg101 null mutant mice show defective cell proliferation and early embryonic death (Ruland, J., Sirard, C., Elia, A., MacPherson, D., Wakeham, A., Li. L., de la Pompa, J. L., Cohen, S. N., & Mak, T. W., 2001, *Proc. Natl. Acad. Sci. USA* 98, 1859-1864). The steady state level of Tsg101 normally is controlled post-translationally within a narrow range in cultured murine and human cell lines (Feng, G. H., Lih, C.-J., & Cohen, S. N., 2000, *Cancer Research* 60, 1736-1741) and over-expression from an adventitious promoter, as well as tsg101 deficiency, can lead to neoplastic transformation (Li, L. & Cohen, S. N., 1996, *Cell* 85, 319-329). Regulation of the Tsg101 protein level, which can be affected by the Ub ligase, Mdm2 (Li, L., Liao, J., Ruland, J., Mak, T. W., & Cohen, S. N., 2001, *Proc. Natl. Acad. Sci USA* 98, 1619-1624), requires a C-terminal Tsg101 sequence that is evolutionarily highly conserved in organisms as disparate as humans, *C. elegans, S. pombe,* and *D. melanogaster* (Feng, G. H., Lih, C.-J., & Cohen, S. N., 2000, *Cancer Research* 60, 1736-1741; Bishop N and Woodman P., 2001, J Biol Chem. 276:11735-42).

Stp22p/Vps23, a class E vacuolar protein sorting (vps) protein in *S. cerevisiae,* has been identified as a Tsg101 orthologue and Tsg 101 itself has been implicated in the trafficking of membrane-associated proteins (Bishop N and Woodman P., 2001, J Biol Chem. 276:11735-42; Babst, M., Odorizzi, G., Estepa, E. J. & Emr, S. D., 2000, *Traffic* 1, 242-258; Li, Y., Kane, T., Tipper, C., Spatrick, P. & Jenness, D. D., 1999, *Mol. & Cell. Biol.* 19, 3588-3599). It has also been shown that SL6 cells are defective in sorting of multiple surface-bound proteins (Babst, M., Odorizzi, G., Estepa, E. J. & Emr, S. D., 2000, *Traffic* 1, 242-258).

Citation of references hereinabove shall not be construed as an admission that such references are prior art to the present invention.

3. SUMMARY OF THE INVENTION

The present invention provides methods for identifying peptides in a mammalian Tsg101 protein that bind to the PTAP (SEQ ID NO: 39) motif or L domain of human immunodeficiency virus type I (HIV-1). Such peptides can be used to inhibit Tsg101-HIV Gag binding, and are therefore effective in reducing HIV particle production. In a preferred embodiment of the invention, peptides in a mammalian tsg101 protein are identified by a method comprising (a) measuring a level of HIV viral particles released in a culture of mammalian cells, wherein said mammalian cells comprise an expression construct comprising a portion of the coding sequence of a mammalian tsg101 gene such that said mammalian cells express a gene product encoded by said portion of said coding sequence of said mammalian tsg101 gene and are infected by HIV virus; and (b) comparing the level of HIV viral particles to a level of HIV viral particles released in a culture of control mammalian cells which do not comprise an expression construct comprising a portion of a coding sequence for a mammalian tsg101 gene under similar conditions. In the method, the level of HIV viral particles measured in step (a) compared to the level of HIV viral particles in the culture of control mammalian cells below a predetermined threshold level identify the gene product encoded by the portion of the coding sequence of the mammalian tsg101 gene as effective in reducing HIV particle production. In a preferred embodiment, the level of HIV viral particles released in a culture of mammalian cells and the level of HIV viral particles released in a culture of control mammalian cells are represented by measured levels of particle associated p24. In preferred embodiments of the invention, the predetermined threshold level is a two-fold, four-fold, 90%, 95%, 99%, or 99.5% reduction of the level of HIV viral particles measured in step (a) compared to the level of HIV viral particles of the culture of control mammalian cells.

In another preferred embodiment of the invention, peptides in a mammalian tsg101 protein are identified by a method comprising (a) measuring a level of HIV viral particle released in a culture of mammalian cells, wherein the mammalian cells comprise (i) an expression construct comprising a portion of the coding sequence of a mammalian tsg101 gene and (ii) an expression construct comprising the HIV gag coding sequence such that the mammalian cells express a gene product encoded by the portion of the coding sequence of the mammalian tsg101 gene and a gene product encoded by the HIV gag gene; and (b) comparing the level of HIV viral particle released to a level of HIV viral particle released in a culture of control mammalian cells under similar conditions, wherein the control mammalian cells comprise one or more expression constructs comprising the HIV gag coding sequence such that the mammalian cells express a gene product encoded by the HIV gag gene, and wherein the control mammalian cells do not comprise an expression construct comprising a portion of a coding sequence for a mammalian tsg101 gene. In still another preferred embodiment of the invention, peptides in a mammalian tsg101 protein are identified by a method comprising (a) measuring a level of HIV viral particles released in a culture of mammalian cells, wherein the mammalian cells comprise (i) an expression construct comprising a portion of the coding sequence of a mammalian tsg101 gene and (ii) one or more expression constructs comprising the HIV gag, pol, and rev coding sequences such that the mammalian cells express a gene product encoded by the portion of the coding sequence of the mammalian tsg101 gene and gene products encoded by the HIV gag, pol and rev genes; and (b) comparing the level of HIV viral particles released to a level of HIV viral particles released in a culture of control mammalian cells under similar conditions, wherein the control mammalian cells comprise one or more expression constructs comprising the HIV gag, pol, and rev coding sequences such that the mammalian cells express gene products encoded by the HIV gag, pol and rev genes, and wherein the control mammalian cells do not comprise an expression construct comprising a portion of a coding sequence for a mammalian tsg101 gene. In these embodiments, the level of HIV viral particles measured in step (a) compared to the level of HIV viral particles released in the culture of control mammalian cells below a predetermined threshold level identify the gene product encoded by the portion of the coding sequence of the mammalian tsg101 gene as effective in reducing HIV particle production. In a preferred embodiment, the level of HIV viral particles released in a culture of mammalian cells and the level of HIV viral particles released in a culture of control mammalian cells are represented by measured levels of particle associated p24. In preferred embodiments of the invention, the predetermined threshold level is a two-fold, four-fold, 90%, 95%, 99%, or 99.5% reduction of the level of particle associated p24 measured in step (a) compared to the level of particle associated p24 of the culture of control mammalian cells.

The invention also provides a method for identifying a peptide or fragment derived from a mammalian Tsg101 protein, which is effective in reducing production of retroviral particles, e.g., particles of a lentivirus, including but not limited to HIV-1 and HIV-2, Simian Immunodeficiency Virus (SIV). The method comprises identifying a peptide that binds to a peptide comprising the PTAP (SEQ ID NO: 39) motif of a retroviral protein, e.g., a HIV Gag protein. In a preferred embodiment, the peptide comprising the PTAP (SEQ ID NO: 39) motif is the peptide of SEQ ID NO: 4. In another preferred embodiment, the peptide comprising the PTAP (SEQ ID NO: 39) motif is a HIV Gag protein.

The invention also provides a method for identifying a peptide comprising a PTAP (SEQ ID NO: 39) motif, which is effective in reducing production of retroviral particles, e.g., particles of a lentivirus, including but not limited to HIV-1 and HIV-2, Simian Immunodeficiency Virus (SIV). The method comprises identifying a peptide identifying a peptide comprising a PTAP (SEQ ID NO: 39) motif which binds to a TSG101 protein. In a preferred embodiment, the peptide comprises peptide comprises the sequence of SEQ ID NO: 4.

The invention also provides the peptides identified by the method of the invention and to method of using such peptides for treating HIV infection.

4. BRIEF DESCRIPTION OF THE FIGURES

Figure 1B:
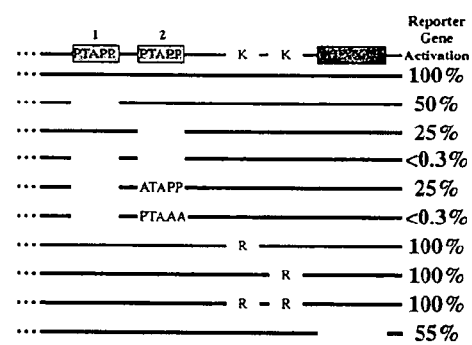

FIG. 1. Identification of the region in PR55$^{Gag}$ required for Tsg101 binding using the 2-hybrid assay. Reporter gene activation was quantified by determination of β-galactosidase units. FIG. 1A, The interaction of Gag and p1-p6 with Tsg101. β-Galactosidase activity of Gag and p1-p6 were equivalent in two independent trials. FIG. 1B, The interaction of p1-p6 with Tsg101 (taken as 100%) ranged from ~10 to 30β-galactosidase units in twenty independent trials. Negative interactions were equivalent to that obtained when p1-p6 was co-transformed with vector lacking Tsg101 (<0.3 units). The figure shows averaged values obtained for mutants in six independent trials as a percentage of the wild-type interaction +/−1%. PTAPP, ATAPP AND PTAAA dislcosed as SEQ ID NOS 3 and 45-46, respectively.

Figures 2A, 2B:
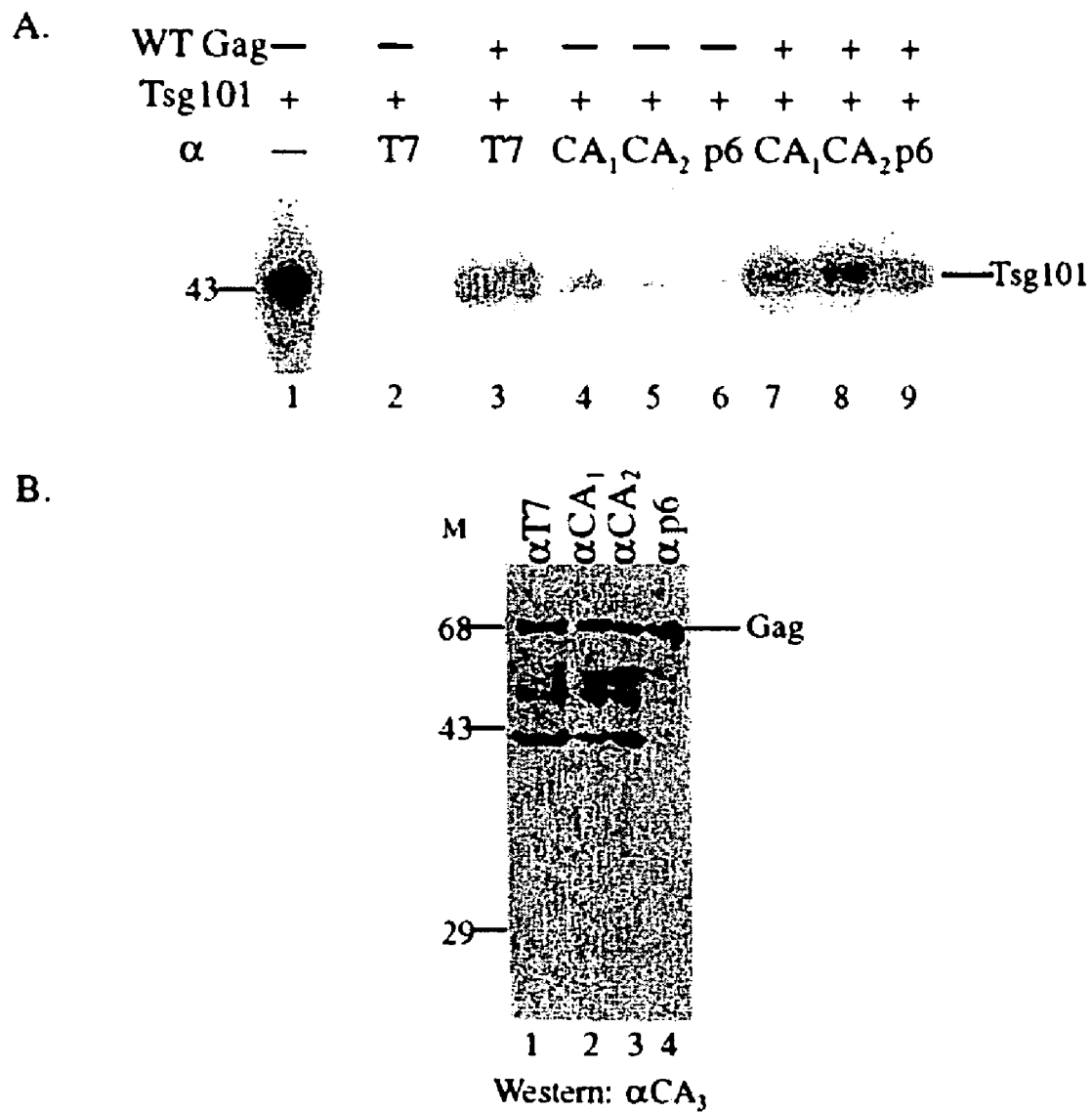

FIG. 2. Binding of PR55$^{Gag}$ and Tsg101 in vitro. FIG. 2A, Autoradiography to detect immune-captured radiolabeled Tsg101. Lane 1, Tsg101 synthesized in RRL. Lanes 2 to 9, Determination of binding of radioactive Tsg101 to unlabeled Pr55GS bound to anti-T7 (lane 3), anti-CA (lanes 7, 8), or anti-p6 (lane 9) IgG immobilized on protein A beads. Antibodies are as defined in Materials and Methods. The amount of RRL used in lanes 2 to 9 was 5-fold greater than the amount used in lane 1. FIG. 2B, Confirmation of the presence of PR55$^{Gag}$ on the beads by Western analysis. A monoclonal antibody against an antigenic site in the CA domain was used to visualize the Gag proteins immunoprecipitated with the antibodies used in A. Molecular weight markers (kDa) are on the left of the panels.

FIG. 3. Co-immune precipitation of PR55$^{Gag}$ and Tsg101 from cytoplasmic extracts. FIG. 3A, Total cytoplasmic extract. Extracts Were prepared from cells transfected with rev (lane 1), rev, gag and pol (lane 2), or rev, gagΔp6 and pol (lane 3). FIG. 3B, Immunoprecipitation with anti-Tsg101 monoclonal antibody using extracts of cells transfected with rev (lane 1); rev, wild-type gag and pol (lane 2); or rev, gag$^{Δp6}$ and pol (lane 3) as detected by the anti-NC polyclonal antibody. The blot was re-probed with an anti-Tsg101 polyclonal antibody to confirm the presence of Tsg101 in the immune-precipitates (lanes 4-6). FIG. 3C, Immunoprecipitation with anti-CA polyclonal antibody using extracts from cells transfected with rev (lane 1) or rev, gag and pol (lane 2) as detected by anti-Tsg101 monoclonal antibody. The blot was re-probed with anti-CA monoclonal antibody to confirm the presence of Gag in the immune-precipitate (lanes 3, 4). Molecular weight markers (kDa) are on the left of the panels.

Figures 4A, 4B, 4C:
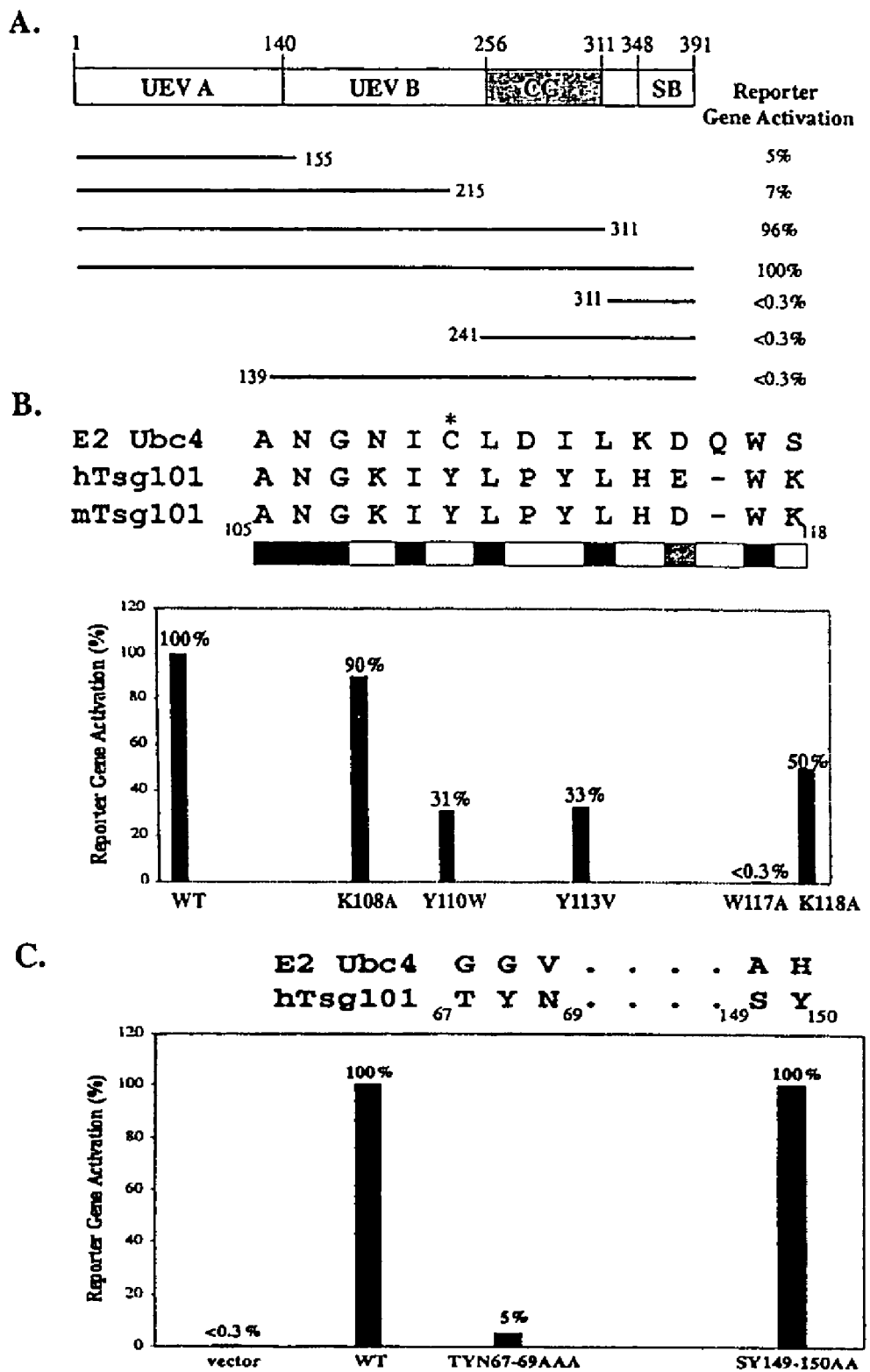

FIG. 4. Identification of the region in Tsg101 required for Pr55$^{Gag}$ binding. Truncation (FIG. 4A) and substitution (FIGS. 4B and 4C) mutants of Tsg101 were tested in the 2-hybrid assay for interaction with the p1-p6 fusion protein. The figure shows averaged values as a percentage of the wild-type interaction with +/−2-6% error. Notations are as in legend to FIG. 1. E2 Ubc4, hTsg101, mTsg101 sequences disclosed as SEQ ID NOS 47-49, respectively.

Figures 5A, 5B, 5C, 5D:
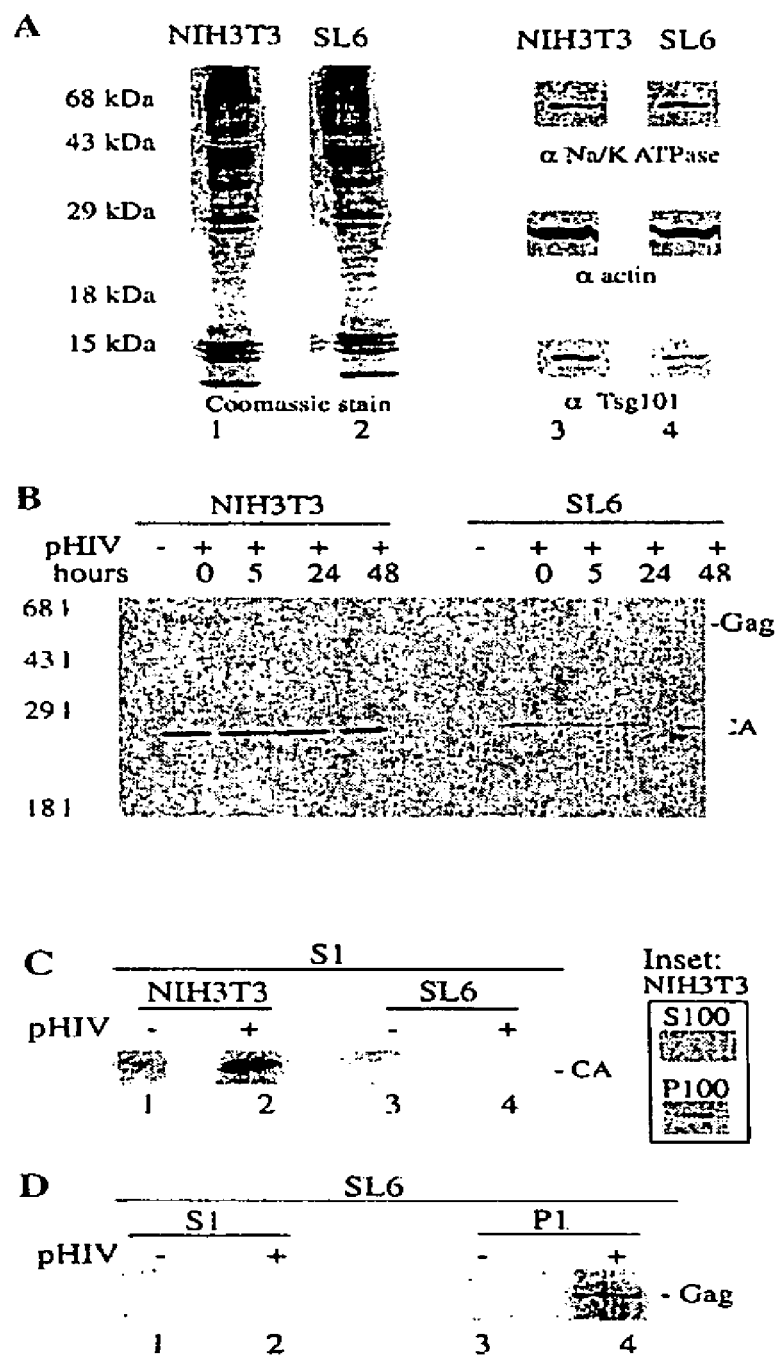

FIG. 5. Effects of Tsg101 deficiency on virus production and cellular localization. FIG. 5A, NIH 3T3 and SL6 lysates prepared from gag-transfected cells were separated by SDS-PAGE, stained by Coomassie blue for total protein (lanes 1 & 2), and analyzed by Western blotting for Na$^+$K$^+$ATPase, actin, and Tsg101 (lanes 3 & 4). FIGS. 5B-5D, Western blots of (5B) viral particles; (5C) S1 extracts of NIH 3T3 and SL6 cells; Inset, S100 (lane 1) and P100 (lane 2) fractions of pHIV-transfected NIH 3T3 cells; (5D) S1 and P1 extracts of SL6 cells. The blots were probed with anti-CA rabbit serum (FIGS. 5B and 5C) or anti-NC goat antiserum. (FIG. 5D). Equivalent samples for Western analysis were determined by Biorad assay.

Figure 6A:
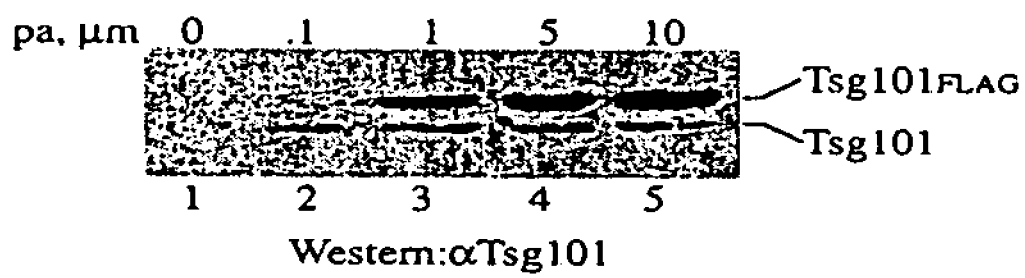
Figure 6B:
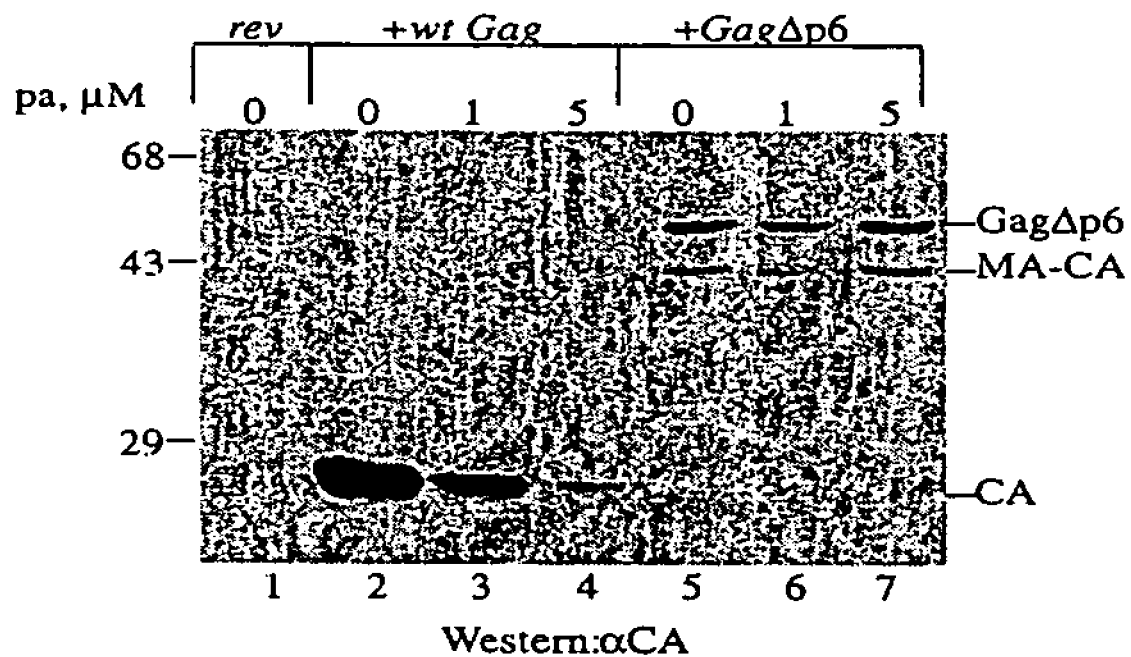

FIG. 6. Effect of wild-type Tsg101 over expression on release of HIV-1 particles. FIG. 6A, Induced expression of wild-type Tsg101$_{FLAG}$. S1 fractions prepared from transfected COS-1 cells were analyzed by Western blotting with anti-Tsg101 antibody. pa, ponasterone inducer. FIG. 6B, Effect of Tsg101-FLAG over expression on HIV-1 release from COS-1 cells, analyzed by Western blotting of particles with anti-CA antibody. Migration positions of molecular size markers are indicated on the left.

Figures 7A, 7B:
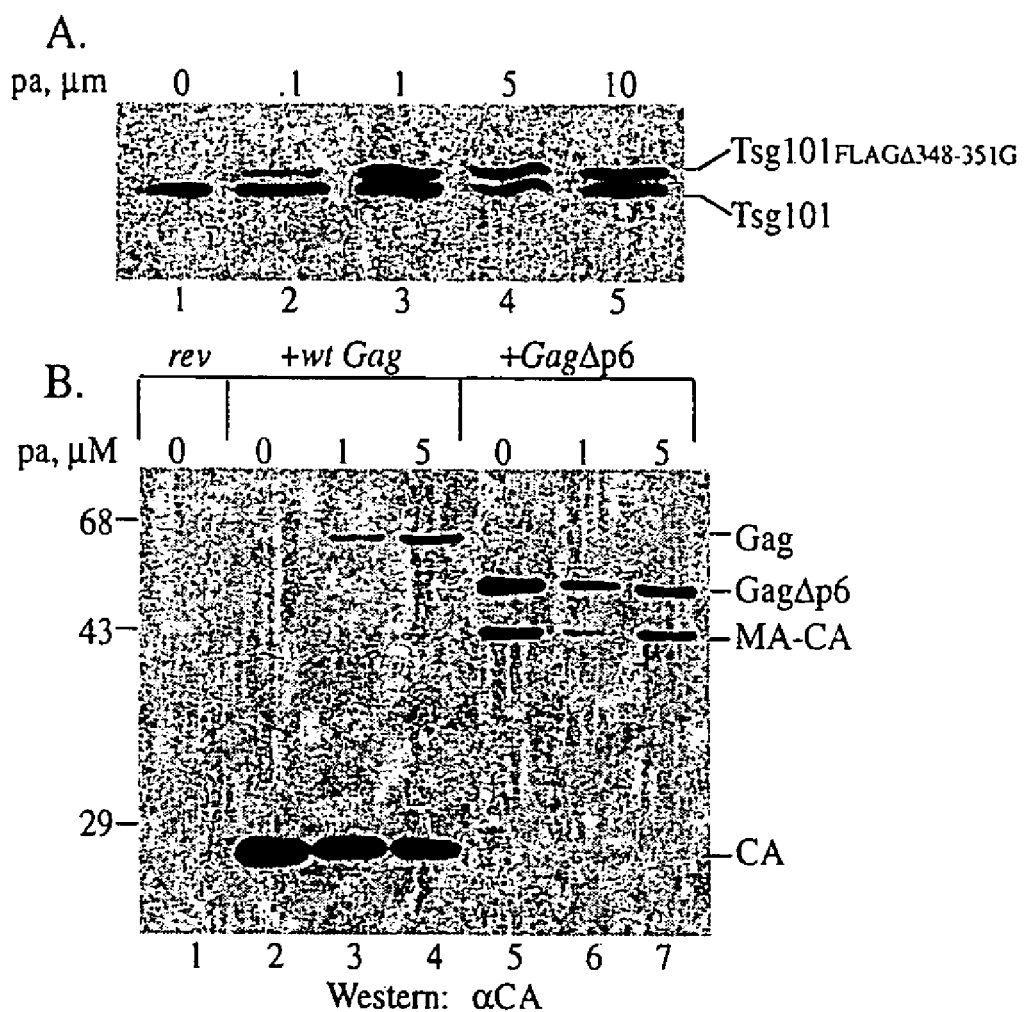

FIG. 7. Effect of mutated Tsg101 over expression on release of HIV-1 particles. FIG. 7A, Induced expression of Tsg101$_{FLAGΔ348-351G}$. FIG. 7B, Effect of Tsg101-FLAG over expression on HIV-1 particle production. S1 fractions and viral particles were analyzed as described in the legend to FIG. 6.

FIG. 8. Immunoprecipitation of viral proteins in cytoplasmic extracts with anti-Tsg101 antibody. FIG. 8A, Cytoplasmic extracts, prepared from mock-(lanes 1 & 2) and gag-(lanes 3 & 4) transfected COS-1 cells expressing FLAG-tagged wild-type (lanes 1 & 3) or mutated (lanes 2 & 4) Tsg101, were analyzed by Western blotting with anti-p6 antibody. Expression was induced using 2 μg DNA encoding tsg101 and 5 μM pa. FIGS. 8B-8D, The extracts were immunoprecipitated with anti-Tsg101 rabbit polyclonal antibody and probed for proteins with (8B) anti-p6 antibody; (8C) anti-FLAG antibody; and (8D) antiTsg101 mouse monoclonal antibody.

Figures 9A, 9B, 9C:
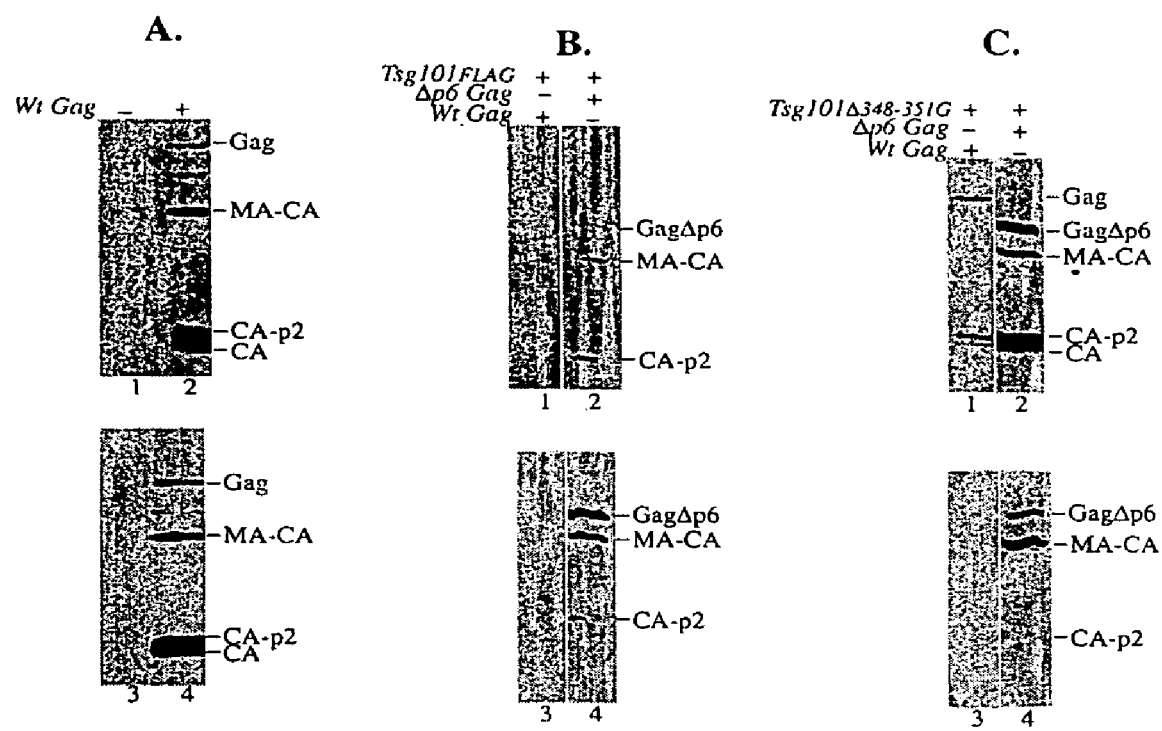

FIG. 9. Effect of Tsg101 over expression on intracellular steady-state level of viral proteins. Cytoplasmic extracts were prepared from cells expressing Rev-(FIG. 9A, lanes 1 & 3), wild-type Gag- (FIGS. 9B & 9C, lanes 1 & 3), or GagΔp6-(FIGS. 9B & 9C, lanes 2 & 4) and FLAG-tagged wild-type (FIG. 9B) or mutated (FIG. 9C) Tsg101. S1 (lanes 1 & 2) and P1 (lanes 3 & 4) fractions were analyzed by Western blotting with anti-CA antibody.

5. DETAILED DESCRIPTION OF THE INVENTION

In accordance with the present invention, it has been discovered that the PTAP (SEQ ID NO: 39) motif or L domain of human immunodeficiency virus type I (HIV-1), which is located in the C-terminal p6 region of the Gag precursor polyprotein, binds to the protein product of the tsg101 gene in vitro and in the cytoplasm of transfected cells. The present invention provides an assay for testing molecules, e.g., peptides comprising at least four contiguous amino acids of the PTAP (SEQ ID NO: 39) motif, and which molecules inhibit Tsg101-HIV Gag binding. Preferably, the assay of the invention is used to identify molecules, e.g., peptides, which can achieve a two-fold, four-fold, more than 90%, more than 95%, more than 99%, or more than 99.5% reduction of HIV viral release. Molecules, e.g., peptides, identified by the assay may be used as therapeutic compositions for treating patients infected with HIV-1 or other retrovirus.

It has also been surprisingly found that perturbation of the steady-state level of Tsg101 protein by under- or over-expression of the Tsg101 protein negatively affects release of HIV-1 virus-like particles from murine and primate cells. The present invention therefore provides a pharmaceutical composition comprising one or more pharmaceutically acceptable carriers or diluents and a mammalian Tsg101 protein. In another aspect of the invention, assays are provided for identifying fragments of a mammalian Tsg101 protein which are effective in reducing HIV particle production. As used herein, "HIV particle" encompasses both mature and immature virus-like particles. A fragment of Tsg101, herein referred to as a "peptide" of Tsg101, identified by a subject assay as effective in reducing HIV particle production, is useful as a therapeutic composition for treating a patient infected with HIV-1 or other retrovirus. Pharmaceutical compositions comprising one or more subject peptides and one or more pharmaceutically acceptable carriers or diluents are therefore also provided.

Thus, in one embodiment of the present invention, there is provided a method for identifying a peptide derived from a mammalian Tsg101 protein, which peptide is effective in reducing HIV particle production. The method comprises the steps of: (a) introducing into a mammalian cell or cells, a first expression construct wherein the first expression construct comprises a portion of the coding sequence for a mammalian tsg101 gene; (b) introducing into the same mammalian cell or cells either HIV virus or one or more expression vectors comprising the HIV gag, pol and rev coding sequences; (c) incubating the transfected mammalian cell or cells in a suitable media for a sufficient time and under conditions sufficient to obtain a mammalian cell culture wherein the mammalian cells express a gene product encoded by the portion of a coding sequence for a mammalian tsg101 gene, and gene products encoded by the HIV gag, pol, and rev genes. In the case where one or more expression vectors comprising the HIV gag, pol, and rev genes, are used to transfect a mammalian cell or cells, the level of particle associated p24 (capsid protein) may be measured. A finding of a reduced level of particle associated p24, when compared to a control mammalian cell culture which has not been transfected with the expression construct comprising a portion of the coding sequence for a mammalian tsg101 gene, correlates with the identification of a Tsg101 peptide effective in reducing HIV particle formation. In the case where HIV virus is added to the mammalian cell or cells, particle associated p24 may be measured and a correlation made, as described above. Alternatively, when HIV virus is added to the mammalian cell or cells, HIV particles released from the cells may be quantified. A finding of a reduction in HIV particle production, when compared to a control mammalian cell culture which has not been transfected with the expression construct comprising a portion of the coding sequence for a mammalian tsg101 gene, correlates with the identification of a peptide effective in reducing HIV particle production.

In another embodiment of the invention, peptides in a mammalian tsg101 protein are identified by a method comprising (a) measuring a level of HIV viral particles released in a culture of mammalian cells, wherein said mammalian cells comprise an expression construct comprising a portion of the coding sequence of a mammalian tsg101 gene such that said mammalian cells express a gene product encoded by said portion of said coding sequence of said mammalian tsg101 gene and are infected by HIV virus; and (b) comparing the level of HIV particles to a level of HIV particles released in a culture of control mammalian cells which do not comprise an expression construct comprising a portion of a coding sequence for a mammalian tsg101 gene under similar conditions. In the method, the level of HIV particles measured in step (a) compared to the level of HIV particles of the culture of control mammalian cells below a predetermined threshold level identify the gene product encoded by the portion of the coding sequence of the mammalian tsg101 gene as effective in reducing HIV particle production.

In still another embodiment of the invention, peptides in a mammalian tsg101 protein are identified by a method comprising (a) measuring a level of HIV viral particle released in a culture of mammalian cells, wherein the mammalian cells comprise (i) an expression construct comprising a portion of the coding sequence of a mammalian tsg101 gene and (ii) an expression construct comprising the HIV gag coding sequence such that the mammalian cells express a gene product encoded by the portion of the coding sequence of the mammalian tsg101 gene and a gene product encoded by the HIV gag gene; and (b) comparing the level of HIV viral particle released to a level of HIV viral particle released in a culture of control mammalian cells under similar conditions, wherein the control mammalian cells comprise one or more expression constructs comprising the HIV gag coding sequence such that the mammalian cells express a gene product encoded by the HIV gag gene, and wherein the control mammalian cells do not comprise an expression construct comprising a portion of a coding sequence for a mammalian tsg101 gene.

In still another embodiment of the invention, peptides in a mammalian tsg101 protein are identified by a method comprising (a) measuring a level of HIV particles released in a culture of mammalian cells, wherein the mammalian cells comprise (i) an expression construct comprising a portion of the coding sequence of a mammalian tsg101 gene and (ii) one or more expression constructs comprising the HIV gag, pol, and rev coding sequences such that the mammalian cells express a gene product encoded by the portion of the coding sequence of the mammalian tsg101 gene and gene products encoded by the HIV gag, pol and rev genes; and (b) comparing the level of HIV particles released to a level of HIV particles released in a culture of control mammalian cells under similar conditions, wherein the control mammalian cells comprise one or more expression constructs comprising the HIV gag, pol, and rev coding sequences such that the mammalian cells express gene products encoded by the HIV gag, pol and rev genes, and wherein the control mammalian cells do not comprise an expression construct comprising a portion of a coding sequence for a mammalian tsg101 gene. In these embodiments, the level of HIV particles measured in step (a) compared to the level of HIV particles released in the culture of control mammalian cells below a predetermined threshold level identify the gene product encoded by the portion of the coding sequence of the mammalian tsg101 gene as effective in reducing HIV particle production.

In preferred embodiments of the invention, the peptide identified causes at least a two-fold, four-fold, 90%, 95%, 99%, or 99.5% reduction of the level of HIV particles released or reduction of the level of particle associated p24 in the culture.

In an alternative embodiment, a method for identifying a peptide derived from a mammalian Tsg101 protein, which peptide is effective in reducing HIV particle production may be performed as described above except that instead of using an expression construct comprising a portion of a coding sequence for a mammalian tsg101 gene, random fragments (peptides) of a mammalian Tsg101 protein are generated and added to a mammalian cell or cells which cells are also infected with HIV or transfected with one or more expression constructs comprising the HIV gag, pol, and rev coding sequences. Tsg101 fragments (peptides) may be introduced into mammalian cells using well known methods of permeation. It will be apparent to a person of ordinary skill in the art that this embodiment is also applicable for identifying other molecules that is effective in reducing HIV or other viral particle production. Therefore, in another aspect of the invention, a method for identifying molecules that is effective in reducing HIV or other viral particle production is provided.

In another embodiment, the invention provides a method for identifying a peptide or fragment derived from a mammalian Tsg101 protein, which is effective in reducing production of retroviral particles, e.g., particles of a lentivirus, including but not limited to HIV-1 and HIV-2, Simian Immunodeficiency Virus (SIV). The method comprises identifying a peptide that binds to a peptide comprising the PTAP (SEQ ID NO: 39) motif of a HIV Gag protein. In a preferred embodiment, the peptide comprising the PTAP (SEQ ID NO: 39) motif is the peptide of SEQ ID NO: 4. In another preferred embodiment, the peptide comprising the PTAP (SEQ ID NO: 39) motif is a HIV Gag protein. Any standard method known in the art for identifying peptide binding can be used.

Preferably, the portion of a coding sequence for a mammalian tsg101 gene includes at least a portion of the UEV A domain of Tsg101. The UEVA region spans amino acids 1 through 140 of a mammalian Tsg101.

In another preferred embodiment, the mammalian cells are primate cells. Mammalian 25 cells useful for practicing the invention include but are not limited to green monkey kidney cells, human HeLa cells, and human 293 cells. These and other mammalian cell lines are available from a variety of sources such as the American Type Culture Collection (ATCC), Manassas, Va.

A mammalian tsg101 gene may be obtained from any mammalian cell. For example, a human tsg101 gene may be isolated from B cells or a B cell library (Durfee T., et al. 1993, *Genes Dev.* 7:555-569). Similarly, a mouse or other mammalian tsg101 gene may be isolated from B cells or a B cell library. The nucleotide sequence and corresponding amino acid sequence for a human tsg101 gene and a mouse tsg101 gene are known. See, e.g., Li, L. et al. (1997) *Cell* 88:143-154, which is incorporated by reference herein. Relevant mouse and human tsg101 genes are also disclosed in U.S. Pat. Nos. 5,807,995; 5,892,016; 5,679,523; and 5,891,668, which are also incorporated by reference herein. The aforementioned disclosures, as well as any other publications mentioned herein, are incorporated by reference as if fully set forth. The mouse Tsg101 protein is also set forth herein as SEQ ID NO:1. The human Tsg101 protein is set forth herein as SEQ ID NO:2.

Peptides derived from a mammalian Tsg101 protein may be obtained by truncating the 3', 5' or both 3' and 5' end of the tsg101 coding sequence by genetic manipulation. In vitro mutagenesis is helpful for introducing convenient restriction sites. There are various commercially available kits particularly suited for this application such as the T7-Gene in vitro Mutagenesis Kit (USB, Cleveland, Ohio) and the QuikChange Site Directed Mutagenesis Kit (Stratagene, San Diego, Calif.). Alternatively, PCR primers can be defined to allow direct amplification of a particular portion of a tsg101 coding sequence. (See, e.g., Example 1). Preferably, the portion of the tsg101 coding sequence corresponds to a portion of the UEVA region. A portion of the coding sequence for a mammalian tsg101 gene may be inserted into many different types of expression vectors. For example, the expression construct comprising a portion of the coding sequence for a mammalian tsg101 gene may be any expression construct which functions in mammalian cells. In a more preferred embodiment, the coding sequence for a portion of a tsg101 gene is placed in a vector which encodes both monomers of a heterodimeric ecdysone-inducible receptor, that together with the hormone ecdysone or ecdysone analogue such as pronasterone, form a transcriptional activator complex that binds the promoter driving tsg101 expression.

Expression vectors encoding different HIV genes are widely known and available. For example, tgp-RRE-r (Smith et al. 1990 *J. Virol.* 64:2743-2750) is an expression vector comprising both the gag and pol coding regions. pCMV-rev is an expression vector comprising the HIV-1 rev gene. Rev is an HIV-1 encoded protein required for expression of gag and pol. In mammalian host cells, a number of expression systems using elements from viral and cellular DNA may be utilized for expressing a portion of a tsg101 coding sequence and the HIV gag, pol and rev coding sequences.

Any known method may be used to quantify HIV particles released from the cells. Quantification of HIV particles released from the cells may be performed using different methods such as by p24 ELISA or by infectivity assay as described in Flint, S. J. et al., 2000, *Principles of Virology: Molecular Biology, Pathogenesis and Control,* ASM Press, Washington, D.C. Virus particles may first be isolated from culture media or supernatant by passing through a filter such as e.g., a 0.22 μm filter followed by ultracentrifugation through a 20% sucrose cushion. Following disruption of HIV particles with a suitable detergent such as e.g., 1% SDS, p24 protein may be separated by electrophoresis through a 12.5% SDS polyacrylamide gel, followed by Western blotting using antibodies specific to p24 such as anti-CA rabbit polyclonal antibody raised against a native form of the CA protein (Ehrlich, L. S., et al., 1990 *AIDS Res & Hum. Retro.* 6:1169-1175), or anti-CA mouse monoclonal antibody (NEN-DuPont).

In accordance with the present invention, there are provided Tsg101 peptides which comprise at least about four contiguous amino acids of a mammalian Tsg101 protein, which are effective in reducing HIV particle production and which are identified by a subject assay hereinbefore described. Preferably, a subject peptide comprises at least about 5 contiguous amino acids which are effective in reducing HIV particle production and which are identified by a subject assay hereinbefore described. Even more preferred is a peptide comprising at least about 6 contiguous amino acids and which is effective in reducing HIV particle production and which are identified by a subject assay hereinbefore described. In a most preferred embodiment, a subject peptide comprises at least about 7 contiguous amino acids. Thus, for example, a subject peptide may comprise at least about 4, preferably at least about 5, more preferably at least about 6, and most preferably, at least about 7 contiguous amino acids of the amino acid sequence as set forth in SEQ ID NO:1 or SEQ ID NO:2. Preferably, a subject peptide is derived from or includes part of the UEV A domain of a mammalian Tsg101 protein. As used herein, "peptide" refers to a fragment of a Tsg101 protein comprising at least about four amino acids. Thus, a peptide may comprise as little as about four amino acids of a mammalian Tsg101 protein. A subject peptide may also comprise anywhere from about four to about 140 contiguous amino acids from a mammalian Tsg101 protein. Amino acid sequences larger than about 140 amino acids are referred to herein as Tsg101 fragments. Additionally, analogs, homologs, fragments, chemical derivatives, and pharmaceutically acceptable salts of the subject peptides are included within the scope of the term "peptide". A subject peptide may also comprise a repetition of an amino acid unit.

By "analogs" is meant substitutions or alterations in the amino acid sequences of a subject peptide, which substitutions, or alterations, e.g., additions and deletions of amino acid residues, do not abolish the property of reducing HIV particle production or inhibiting Tsg101-Gag binding. Thus, an analog may comprise a peptide having a substantially identical amino acid sequence to a subject peptide and in which one or more amino acid residues have been conservatively substituted with chemically similar amino acids.

In addition to the recombinant DNA techniques described above for preparing a subject peptide, a peptide of the present invention may be synthesized by a number of known techniques. For example, a peptide may be prepared using the solid-phase synthetic technique initially described by Merrifield, in *J. Am. Chem. Soc.* 85:2149-2154 (1963). Other peptide synthesis techniques may be found in M. Bodanszky et al. *Peptide Synthesis,* John Wiley & Sons, 2d Ed. (1976) and other references readily available to skilled artisans. A summary of polypeptide synthesis techniques can be found in J. Stuart and J. D. Young. *Solid Phase Peptide Synthesis,* Pierce Chemical Company, Rockford, Ill., (1984). Peptides may also be synthesized by solution methods as described in *The Proteins,* Vol. II, 3d Ed., Neurath, H. et. al., Eds., p. 105-236, Academin Press, New York, N.Y. (1976). Appropriate protective groups for use in different peptide syntheses are described in the above-mentioned texts as well as in J. F. W. McOmie, *Protective Groups in Organic Chemistry,* Pelenu Press, New York, N.Y. (1973).

The peptides of the present invention might also be prepared by chemical or enzymatic cleavage from larger portions of a mammalian Tsg101 protein or from an entire mammalian Tsg101 protein. The peptides of the present invention are preferably chemically synthesized by the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

The preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is added, and so forth. After all the desired amino acids have been linked in the proper sequence, any remaining terminal and side group protecting groups including the solid support are removed sequentially or concurrently to yield the final peptide.

In still another aspect of the invention, there is provided a method for identifying a peptide comprising at least four contiguous amino acids of the HIV-1 late (L) domain and which peptide inhibits interaction between a Tsg101 protein and HIV Gag. The HIV-1 late L domain is made up of the amino acid sequence PTAPP (SEQ ID NO: 3), which is also referred to as the PTAPP (SEQ ID NO: 3) motif. Thus, a peptide identified by the method will have at least four contiguous amino acids of the PTAPP (SEQ ID NO: 3) motif and may also include additional amino acids on either or both the amino terminal and carboxy terminal ends. Preferably, a peptide identified by the method will comprise at least seven amino acids, including the PTAPP (SEQ ID NO: 3) motif. More preferably a peptide identified by the method will include at least four amino acids of the PTAPP (SEQ ID NO: 3) motif and one or more amino acids which naturally flank the PTAPP (SEQ ID NO: 3) motif. PTAPP (SEQ ID NO: 3)-derived peptides may embody repetition of the five amino acid, PTAPP (SEQ ID NO: 3) motif. The amino acids which flank the PTAPP (SEQ ID NO: 3) motif are indicated below (L domain indicated in bold).

ALQSRPEPTAPPEES (SEQ ID NO: 4)

A method for identifying a peptide comprising the HIV-1 Gagp6 late (L) domain and which peptide inhibits interaction between a Tsg101 protein and HIV Gag comprises the following steps. First, a peptide comprising the HIV-1 Gag or HIV-1 Gagp6 late (L) domain is immobilized on a solid support or surface such as a bead, plate, slide, or microtiter dish. Immobilization may be achieved utilizing specific anti Gag or HIV Gagp6 late domain antibodies or other chemical linkers such as, e.g., UV cross linkers. Both an experimental and control run are performed and thus, at least two separate solid supports or surfaces (i.e., a first and second solid support or surface) have the HIV-1 Gag or HIV-1 Gagp6 late (L) domain immobilized thereon (e.g., one column for the experimental run, and one column for the control run). A first (experimental) reaction mixture comprising labeled Tsg101 protein, buffer, and a peptide which comprises the HIV-1 Gagp6 late (L) domain is incubated at about 4 C for a sufficient time. A second (control) reaction mixture comprising labeled TSG101 and a buffer is also incubated at about 4 C for a sufficient time. Preferably, a sufficient time is about 60 minutes. The first (experimental) reaction mixture is added to the first solid support or surface and incubated in a liquid phase for a sufficient time at about 4 C. Likewise, the second (control) reaction mixture is added to the second solid support or surface and incubated in a liquid phase for a sufficient time at about 4 C. Preferably, a sufficient time is about 60 minutes. Next, the first solid support or surface is separated from the liquid phase to obtain a first solid phase. Likewise, the second solid support or surface is separated from the liquid phase to obtain a second solid phase. The amount of labeled Tsg 101 in the first solid phase and in the second solid phase is then determined. A decrease in the amount of labeled TSG101 in the first solid phase when compared to the amount of labeled Tsg101 in the second solid phase correlates with the identification of a peptide comprising the HIV-1 Gagp6 late (L) domain, which peptide inhibits interaction between a Tsg101 protein and HIV Gag. Appropriate antibodies which may be linked to the immobilized peptide comprising the HIV-1 Gag or HIV-1 Gagp6 late (L) domain include anti-p6 rat monoclonal antibody (ABI) and anti Gag CA (NEN-Dupont).

The invention also provides a method for identifying a peptide comprising a PTAP (SEQ ID NO: 39) motif, which modulates or inhibits interaction between a Tsg101 and a PTAP (SEQ ID NO: 39) or related motif of a viral protein which the Tsg101 interacts with. The peptide can be used for reducing production of virus particles, e.g., particles of a lentivirus, including but not limited to HIV-1 and HIV-2, Simian Immunodeficiency Virus (SIV). The method comprises identifying a peptide comprising a PTAP (SEQ ID NO: 39) motif which binds to a TSG101 protein. In a preferred embodiment, the peptide comprises the sequence of SEQ ID NO: 4. The method is also applicable for identifying other molecules that modulate or inhibit interaction between a Tsg101 and a PTAP (SEQ ID NO: 39) or related motif of a viral protein which Tsg101 interacts with, e.g., a PTAP (SEQ ID NO: 39) motif of a HIV Gag, e.g., by binding to the active site of the Tsg101 or the viral protein. Therefore, in another aspect of the invention, methods for identifying molecules that modulate or inhibit interaction between a Tsg101 and a PTAP (SEQ ID NO: 39) or related motif of a viral protein are provided. Any standard method known in the art for identifying peptide binding can be used.

Tsg101 may be labeled with a fluorescer, enzyme, chemiluminescer, photosensitizer, suspendable particles, or radioisotope using any of the common commercially available signal producing systems. Alternatively, Tsg101 may be labeled with a tag such as e.g., an antibody, a 6His tag (SEQ ID NO: 40), GST tag, or influenza virus epitope (HA tag). The Tsg101 protein for use in the assay described above may be from a mouse, human or other mammalian protein.

Preferably, a peptide identified by the assay causes at least about a three-fold reduction in Tsg101-HIV Gag interaction. Any of the peptides of the present invention may be used as a therapeutic composition for reducing HIV particle formation or for inhibiting Tsg101-HIV Gag interaction. Preferably, the therapeutic composition is a pharmaceutical composition. Thus, the peptides of the present invention may be administered preferably to a human subject as a pharmaceutical composition containing a therapeutically effective dose of at least one of the peptides according to the invention, together with one or more pharmaceutically acceptable carriers or diluents. The term "therapeutically effective amount" means a dose needed to reduce HIV particle formation or other retrovirus formation or inhibit Tsg101-HIV Gag interaction, depending on mode of action of a subject peptide. Such mode of action is determined by an appropriate assay as hereinbefore described.

When administered intravenously, the peptide compositions may be combined with other ingredients, such as carriers, and/or diluents and/or adjuvants. Typical carriers include a solvent or dispersion medium containing, for example, water buffered aqueous solutions, ethanol, polyols such as glycerol, propylene glycol, polyethylene glycol, suitable mixtures thereof, surfactants or vegetable oils. Isotonic agents such as sugars or sodium chloride may be incorporated in the subject compositions. The peptides may also be covalently attached to a protein carrier, such as albumin, so as to minimize clearing of the peptides from the blood. There are no limitations on the nature of the other ingredients, except that they must be pharmaceutically acceptable, efficacious for their intended administration and should not degrade the activity of the active ingredients of the compositions. The peptide compositions of the invention may also be impregnated into transdermal patches or contained in subcutaneous inserts, preferably in liquid or semi-liquid form so that a therapeutically effective amounts of one or more subject peptides may be time-released into a subject.

When the peptides of the invention are administered orally, the pharmaceutical compositions thereof containing an effective dose of the peptide may also contain an inert diluent such as an assimilable edible carrier and the like, be in hard or soft shell gelatin capsules, be compressed into tablets, or may be in an elixir, suspension, syrup or the like. The subject peptides are thus compounded for convenient and effective administration in pharmaceutically effective amounts with a suitable pharmaceutically acceptable carrier in a therapeutically effective dose.

The precise therapeutically effective amount of peptides to be used in a method of treating a patient infected with HIV will be determined by the practitioner based on the age, weight and/or gender of the subject, severity of the disease state, diet, time and frequency of administration, drug combination(s), and/or reaction sensitivities. It can generally be stated that the peptides should preferably be administered in an amount from about 0.1 to 100,000 micrograms as a dosage amount, up to a total dose of about 1 gram, depending on the route of administration. Since the peptide compositions of the invention will eventually be cleared from the bloodstream, re-administration of the compositions is indicated and preferred.

6. EXAMPLES

The following examples are presented by way of illustration of the present invention, and are not intended to limit the present invention in any way.

6.1. Example 1

In this example, HIV-1 Pr55$^{Gag}$ was used as bait in a yeast 2-hybrid screen and identified Tsg101, the product of a mammalian tumor susceptibility gene, Tsg101 (Li, L. & Cohen, S. N., 1996, Cell 85, 319-329), as a cellular protein that interacts with HIV-I Gag. The example demonstrates that Tsg101 interacted specifically with the p6 region of HIV-1 Gag both in vitro and in the cytoplasm of transfected cells. Two highly conserved Pro residues in the L domain within p6 were critical for Tsg101 binding. Moreover, the altered Ub-binding site in the UEV domain in Tsg101 as well as other residues unique to Tsg101 were determinants of interaction with Gag. These results implicate a specific component of the cellular trafficking machinery in virus budding and maturation.

Ubiquitination appears to be involved in virus particle release from infected cells. Free ubiquitin (Ub), as well as Ub covalently bound to a small fraction of p6 Gag is detected in mature human immunodeficiency virus particles. The p6 region in the Pr55$^{Gag}$ structural precursor polyprotein binds to Tsg101, a putative Ub regulator that is involved in trafficking of plasma membrane-associated proteins. Tsg101 was found to interact with Gag in (i) a yeast 2-hybrid assay, (ii) in vitro co-immune precipitation using purified Pr55$^{Gag}$ and rabbit reticulocyte lysate-synthesized Tsg101, and (iii) in vivo in the cytoplasm of COS cells transfected with gag. The PTAPP (SEQ ID NO: 39) motif (or late (L) domain) within p6, which is required for release of mature virus from the plasma membrane, was the determinant for binding Pr55$^{Gag}$. The N-terminal region in Tsg101, which is homologous to the Ubc4 class of Ub-conjugating (E2) enzymes, was the determinant of interaction with p6. Mutation of Tyr110 in 101, present in place of the active site Cys that binds Ub in E2 enzymes, and other residues unique to Tsg101 impaired p6 interaction indicating that features that distinguish Tsg101 from active E2 enzymes were important for binding the viral protein. The results link L domain function in HJV to the Ub machinery and a specific component of the cellular trafficking apparatus.

Materials and Methods

Plasmid construction. Oligonucleotides and procedures used for PCR and mutagenesis to construct Pr55$^{Gag}$ p1-p6, and Tsg101 GAL4-hybrids for expression in yeast; human Tsg101 for in vitro expression; and Pr55$^{Gag\Delta p6}$ for expression in mammalian cells are described hereinbelow and in Table 1.

Pr55$^{Gag}$ and p1-p6 hybrids for expression in yeast. HIV-1 sequences were amplified by PCR using plasmid gpVI as template to synthesize inserts for ligation into yeast expression vectors pGBT9 or pMA424 and pGAD424. pgpVI encodes Pr55$^{Gag}$ and part of Pol, and an inactivating mutation in the catalytic site of PR ($D_{25}A$) within Pol. The 5' end primer, oligo no.1 in Table 1, and the 3' end primer (no.2) were used to synthesize a PCR fragment of full-length gag. The primers annealed to nt 333 of gag and the end of the PR coding region, respectively. BamHI and BG1II sites were engineered in the insert for ligation into pGBT9 and pGAD424. For the MA-CA insert, we used the same 5' end primer (no.1) and a 3' end primer (no.3) that annealed at position 1421 in the gag gene at the C-terminus of CA. These oligonucleotides contained the restriction sites Bg1II and BamHI respectively. For the CA-p2-NC insert, a 5' primer (no.4) that annealed to the gag gene at position 730 at the N-terminus of CA and a 3' end primer (no.5) complementary to position 1673 of the gag gene at the C-terminus of p1 were used. The PCR product was cut with Bg1II and ligated into the vector at that site. For the p1-p6 insert, a 5' end primer (no.6) that annealed to the gag gene at position 1636 and a 3 end primer (no.7) that annealed at position 2116 in the pci gene were used. The insert obtained spanned the p1-p6 region of Gag in the gag frame and the first ninety-nine amino acids of the pci frame. It lacked the frame-shift site located in the p1 region upstream of nucleotide 1636 so that only expression of the gag frame was obtained. Both oligonucleotides contained Bg1II sites. The Pr55$^{Gag\Delta p6}$ insert was created by restriction digestion at the unique Bg1II site. gag sequences were ultimately placed in the pGBT9 vector background by transferring inserts from pMA424 to pGBT9 using the BamHI and Sa1I sites. Deletions and site-directed mutations in pGBT9-p1-p6 were created by mutagenesis using the Gene Editor (Promega). Mutagenic oligonucleotides (nos.8-15) were used according to the manufacturer's protocol. Mismatch regions, introduced for point mutations leading to amino acid changes or deletion mutations are underlined or indicated by "/", respectively. Double mutations were created using a second selection oligonucleotide (no.13) that obliterates a SnaBI restriction site within the vector. Resistance to SnaBI digestion selected for the mutant plasmids. The double mutant $K_{487,493}R$ was synthesized using the second selection oligonucleotide and the $K_{487}R$ mutagenic oligo (no.11) with the mutant $K_{487}R$ as the template. The double mutant $\Delta PTAPP_{1,2}$(SEQ ID NO: 3) was synthesized using the second selection oligonucleotide and the $\Delta PTAPP_2$mutagenic oligo (no.9), with $\Delta PTAPP_1$(SEQ ID NO: 3) as the template. Point mutations in the second $\Delta PTAPP_1$(SEQ ID NO: 3) motif were synthesized from the mutant $\Delta PTAPP_1$(SEQ ID NO: 3) using the second selection oligo and oligos nos.14 and 15, as indicated in Table 1.

Tsg101 hybrids for expression in yeast. Tsg101, as isolated from a B cell library in a pACT vector, was used as template for PCR of inserts for the yeast two-hybrid system. The inserts were engineered with EcoRI and SalI sites for ligation into pGAD424. For the wild-type tsg101 insert, the forward (5' end) primer (no. 16) was complementary to the beginning of the coding region of Tsg101. The reverse (3' end) primer was no. 17. Truncations at the 3' end were introduced using the tsg101 forward primer (no. 16) and reverse primers nos. 18-20, all with translational stop codons and SalI sites introduced at the downstream terminus of the gene. Truncations at the 5' end were introduced by using the tsg101 reverse primer (no. 17) and forward primers nos. 21-23, each with an EcoRI site introduced before the 5' terminus of the sequence. Site-directed mutations in tsg101 were created using the Gene Editor and oligos nos. 24-28.

In vitro expression. Human tsg101 was subcloned into the BamHI site of the pET3a vector under the control of the T7 promoter (Novagen). The insert was produced by PCR using pACT-tsg101 as template with 5' primer no. 29, which anneals at the position corresponding to amino acid 10 in the protein, and 3' primer no. 30, which anneals to the C-terminus of the coding region.

Pr55$^{Gag\Delta p6}$ for expression in mammalian cells. pgp-RRE-r was used as a template to synthesize three point mutations in the first codon of p6 by PCR, thereby converting it into a stop (ochre) codon. The 5' primer (no. 31) anneals to nucleotides 1637-1687 of BH10 gag and includes a unique Bg1II site. The 3' primer (no. 32) anneals to nucleotides 2655-2682 in the pol gene downstream of a unique EcoRV site. The pgp-RRE-r plasmid and the fragment produced from PCR were cut with Bg1II and EcoRV, and the desired fragments were ligated.

All constructs were confirmed by sequencing using the ABI Prism BigDye Terminator Cycle Sequencing Ready Reaction kit (Perkin-Elmer, Foster City, Calif.) according to the manufacturer's instructions.

See, e.g., Ehrlich, L. S., Fong, S., Scarlata, S., Zybarth, G. & Carter, C., 1996, Biochemistry 35, 3933-3943; Durfee, T., Becherer, K., Chen, P.-L., Yeh, S.-H., Yang, Y., Kilburn, A. E., Lee, W.-H. & Elledge, S. J., 1993, Genes Dev. 7, 555-569; Smith, A. J., Cho, M. I., Hammarskjold, M. L. & Rekosh, D., 1990, J. Virol. 64, 2743-2750; Ratner, L., Hasteline, W., Patarca, R., Livak, K. J., Starcich, B., Josephs, S. F., Doran, E. R., Rafalski, J. A., Whitehorn, E. A., Baumeister, K., et al., 1985, Nature (London) 313, 277-284.

| | PTAPP and (LXX)$_4$ are diclosed as SEQ ID NOS 3 and 41, respectively. | | | |
|---|---|---|---|---|
| Insert | Template | # | Sequence | |
| gag | pgpVI | 1 | GGCTAGAAGGATCCGGATGGGTGCGAGAGCGTCAG | (SEQ ID NO:5) |
| | | 2 | GAAGATCTATTAGAAGTTTAAAGTGC | (SEQ ID NO:6) |
| MA-CA | | 1 | | |
| | | 3 | GAAGATCTCACTACAAAACTCTTGCC | (SEQ ID NO:7) |

-continued

PTAPP and (LXX)$_4$ are diclosed as SEQ ID NOS 3 and 41, respectively.

| Insert | Template | # | Sequence | |
|---|---|---|---|---|
| CA-p2-NC | | 4 | GGAAGATCTCCCCTATAGTGCAGAACATCC | (SEQ ID NO:8) |
| | | 5 | CGGGATCCTTCCCTGGCCTTCCC | (SEQ ID NO:9) |
| p1-p6 | | 6 | GGGAAGATCTGGCCTTCC | (SEQ ID NO:10) |
| | | 7 | GAAGATCTATTAGAAGTTTAAAGTGC | (SEQ ID NO:11) |
| PTAPP$_1$ | pGBT9-p1p6 | 8 | CAGAGCAGACCAGAG/TTTCTTCAGAGCAGACC | (SEQ ID NO:12) |
| PTAPP$_2$ | | 9 | CAGAGCAGACCAGAG/GAAGAGAGCTTCAGG | (SEQ ID NO:13) |
| K$_{487}$R (AAG) | | 10 | CCCCTCAG<u>AG</u>CCAGGAGCC | (SEQ ID NO:14) |
| K$_{493}$R (AAG) | | 11 | GCCGATAGAC<u>AG</u>GGAACTGTATC | (SEQ ID NO:15) |
| (LXX)$_4$ | | 12 | CCGATAGACAAGGAA/AACGACCCCTCGTCAC | (SEQ ID NO:16) |
| K$_{487,493}$R | pGBT9-p1p6$_{K487}$R | 11 | | |
| (TAC) | | 13 | CATTTCCTA<u>TAT</u>GTAGTATATAG | (SEQ ID NO:17) |
| PTAPP$_{1,2}$ | pGBT9-p1p6 PTAPP$_1$ | 9 | | |
| | | 13 | | |
| P$_7$A | pGBT9-p1p6 PTAPP$_1$ | 13 | | |
| (CCA) | | 14 | GACCAGAGG<u>GC</u>AACAGCC | (SEQ ID NO:18) |
| P$_{10,11}$A | | 13 | | |
| (CCA, CCA) | | 15 | CAGAGCCAACAGCC<u>GCAGC</u>ATTTCTTCAGAGC | (SEQ ID NO:19) |
| tsg101 | pACT-tsg101 | 16 | GAATTCATGGCGGTGTCGGAGAGC | (SEQ ID NO:20) |
| | | 17 | GTCGACTCAGTAGAGGTCACTGAG | (SEQ ID NO:21) |
| N-155 | | 16 | | |
| | | 18 | GTCGACTCATGCCTGGTATGGCGG | (SEQ ID NO:22) |
| N-215 | | 16 | | |
| | | 19 | GTCGACTCAGGGACCAACAGTGGTCAC | (SEQ ID NO:23) |
| N-311 | | 16 | | |
| | | 20 | GTCGACTCAGTTTTCAGACTGATTTTCC | (SEQ ID NO:24) |
| 139-C | | 17 | | |
| | | 21 | GAATTCCCTCCAGTCTTCTCTCGTCC | (SEQ ID NO:25) |
| 241-C | | 17 | | |
| | | 22 | GAATTCCGGATGAAGGAGGAAATGGATCG | (SEQ ID NO:26) |
| 311-C | | 17 | | |
| | | 23 | GAATTCAATGATATCGATGAAGTTATCATTCCC | (SEQ ID NO:27) |
| K$_{108}$A (AAG) | pGAD-tsg101 | 24 | GTTGATGCAAATGGG<u>GC</u>GATATATCTTCC | (SEQ ID NO:28) |
| Y$_{110}$W (TAT) | | 25 | AATGGGAAGATA<u>TGG</u>CTTCCTTATCTAC | (SEQ ID NO:29) |
| Y$_{113}$V (TAT) | | 26 | GGGAAGATATATCTTCCT<u>GCT</u>CTACATGAATGG | (SEQ ID NO:30) |
| W$_{117}$A (TGG) | | 27 | CCTTATCTACATGAA<u>GCG</u>AAACACCCACAG | (SEQ ID NO:31) |
| K$_{118}$A (AAA) | | 28 | CTACATGAATGGG<u>GC</u>CACCCACAGTCAG | (SEQ ID NO:32) |

-continued

PTAPP and (LXX)₄ are diclosed as SEQ ID NOS 3 and 41, respectively.

| Insert | Template | # | Sequence | |
|---|---|---|---|---|
| tsg101 | pACT-tsg101 | 29 | GGATCCATGGTGTCCAAGTAC | (SEQ ID NO:33) |
| | | 30 | GGATCCTCAGTAGAGGTCACTGAG | (SEQ ID NO:34) |
| gag p6 | | 31 | GGAAGATCTGGCCTTCCTACAAGGGAAGGCCAGGGAATT | (SEQ ID NO:35) |
| | | 32 | CCATGTATTGATAGATAACTATGTCTG | (SEQ ID NO:36) |

2-hybrid assay. The PR55$^{Gag}$-Tsg101 interaction was identified by a yeast 2-hybrid screen using a human B cell library (Durfee, T., Becherer, K., Chen, P.-L., Yeh, S.-H., Yang, Y., Kilburn, A. E., Lee, W.-H. & Elledge, S. J., 1993, *Genes Dev.* 7, 555-569). Vectors pGBT9 and pGAD424 encoding PR55$^{Gag}$ or Tsg101 sequences as GAL4 activation and binding domain fusion proteins were transformed into *Saccharomyces cerevisiae* Y153 using procedures previously described (Bartel, P. L. & Fields, S., 1995, *Methods Enzymol.* 254, 241-263). Briefly, interactions were detected using a selection for Trp and Leu prototrophy followed by quantitative assay for LacZ activation. True positives were confirmed by demonstrating that they failed to interact with vectors carrying no insert or vectors carrying nonspecific genes (lamin). Proteins were identified after automated sequencing and matching the DNA to a protein sequence in the database. Mapping of the interacting domain was performed using vectors encoding the DNA-binding or activation domain of the yeast GAL4 transcriptional activator protein fused to truncations, deletions or point mutations of the proteins. Interactions were tested in both orientations: The text describes the interactions of the GAL4 DNA-binding domain-Gag or -p1-p6 fusion proteins with the GAL4 activation domain-Tsg101 fusion protein. Expression of all GAL4 fusions was checked by analysis of yeast cell extracts by SDS-gel electrophoresis and Western blotting with an antibody directed against the GAL4 binding domain (Upstate Biochemical) and GAL4 transactivation domain (Santa Cruz).

Cell culture, transfection, and preparation of cytoplasmic extracts. COS-1 cells were cultured in DMEM supplemented with fetal bovine serum to 60% confluency at 37° C. The cells were transfected using the FuGene 6 reagent (Roche) according to the instructions of the manufacturer. At 48 hr post-transfection, the cells were harvested into the media and collected by centrifugation. The pelleted cells were washed with cold PBS, allowed to swell in hypotonic buffer (10 mM Tris, pH 7.4, 1 mM MgCl$_2$; 4° C.) containing protease inhibitors, and disrupted with a Dounce homogenizer (type B pestle). The total lysate was spun for 10 min at 10,000×g at 4° C. to remove unbroken cells, nuclei, and mitochondria.

Immune capture assays. For in vitro assay of Tsg101-Gag interaction, Tsg101 was expressed in rabbit reticulocyte lysate (RRL) from a pET3a-tsg101 construct in the presence of [$^{35}$S]-Met (DuPont NEN) using the TNT T7 Quick Coupled Transcription/Translation System (Promega). Recombinant Pr55$^{Gag}$ produced using the T7 RNA polymerase promoter and containing aa 1-10 of T7 gene 10 at the N-terminus, was purified from an expression strain of *E. coli* (BL21-DE3) as previously described (Ehrlich, L. S., Fong, S., Scarlata, S., Zybarth, G. & Carter, C., 1996, *Biochemistry* 35, 3933-3943). Protein A agarose beads (Pierce), pre-washed with non-denaturating buffer (25 mM Tris, pH 7.4, 150 mM NaCl, 0.5 mM MgCl$_2$, 1 mM CaCl$_2$, 1% IGEPAL (Sigma)) containing protease inhibitors (Roche) were incubated with the appropriate antibody, washed again, and then pre-incubated with Gag. Radiolabeled Tsg101 was then added, and the mixture incubated further at 4° C. in a rotating device for 60 min. The beads were washed, suspended in SDS-PAGE loading buffer and heated at 95° C. for 5 min. Cytoplasmic extracts prepared as described above were also examined for Tsg101-Gag interaction using the same procedure, except that the extract and the antibody-coated Protein A beads were maintained in 10 mM Tris, pH 7.4, 1 mM MgCl$_2$.

Protein detection. Proteins were separated by electrophoresis through a 12.5% SDS polyacrylamide gel. For detection of radiolabeled Tsg101 after electrophoresis, gels were fixed, incubated for 30 min in EN$^3$HANCE (DuPont NEN) autoradiography enhancer for gel fluorography and dried. Radioactive bands were visualized using imaging film (BioMax, Kodak). Gels with non-radioactive samples were transferred to nitrocellulose and analyzed by Western blotting. The following antibodies, as specified in the text, were used: anti-capsid (CA)$_1$ and -CA$_2$ (rabbit polyclonal antibodies raised against native and denatured forms of the CA protein, respectively; Ebbets-Reed, D., 1996, in *Molecular Microbiology*, State University of New York at Stony Brook, Stony Brook, N.Y., pp. 209; Ehrlich, L. S., Agresta, B. E. & Carter, C. A., 1992, *J. Virol.* 66, 4874-4883); anti-CA3 (mouse monoclonal antibody, NEN-DuPont); anti-p6 (rabbit polyclonal against the C-terminal 16 amino acids, S. Campbell, NCI-FCRDC); anti-nucleocapsid (NC, goat polyclonal, A. Rein, NCI-FCRDC); anti-T7 (Novagen); anti-Tsg101$_1$ (monoclonal, Santa Cruz); antiTsg101$_2$ (rabbit polyclonal, obtained from S. Cohen, Stanford U.). Proteins were visualized by chemiluminescence with Lumi-Light (Roche).

Results

Pr55$^{Gag}$ interacts with Tsg101 in the 2-hybrid assay. HIV-1 Pr55$^{Gag}$ was used as bait in the yeast 2-hybrid screen (Bartel, P. L. & Fields, S., 1995, *Methods Enzymol.* 254, 241-263) to identify interacting proteins encoded in a cDNA library derived from human B cells (Durfee, T., Becherer, K., Chen, P.-L., Yeh, S.-H., Yang, Y., Kilburn, A. E., Lee, W.-H. & Elledge, S. J., 1993, *Genes Dev.* 7, 555-569). Approximately 2 million transformants were screened and 2 positives were isolated. Sequencing and matching to recorded entries in the GeneBank database identified one interacting partner as cyclophilin B, which had been previously found to interact with Pr55$^{Gag}$ (Luban, B., Bossolt, K. L., Franke, E. K., Kalpana, G. V. & Goff, S. P., 1993, *Cell* 73, 1067-1078). The other interacting protein was identified as the product of the human tumor susceptibility gene, Tsg101 (Li, L. & Cohen, S. N., 1996, *Cell* 85, 3 19-329; Li, L., Li, X., Francke, U. & Cohen, S. N., 1997, *Cell* 88, 143-154).

Identification of the region in PrSSGat that interacts with Tsg101. To localize the region of Pr55$^{Gag}$ required for interaction with Tsg101, plasmids encoding N- or C-terminally-deleted-Pr55$^{Gag}$ fused to the DNA-binding domain of the yeast GAL4 protein were tested for LacZ reporter gene activation using the 2-hybrid assay. Western analysis, using an antibody against the GAL4 DNA binding domain in the fusion proteins showed that the mutated and wild-type proteins were all expressed at comparable levels. As shown in FIG. 1A, the signal was lost upon deletion of the p1-p6 region of Pr55$^{Gag}$ but was retained in plasmids encoding p1-p6. Thus, interaction with Tsg101 was determined by elements within p1-p6 of Pr55$^{Gag}$.

The p6 region contains the conserved motifs $P_7T/SAP_{10}P_{11}$ (SEQ ID NO: 42) (numbering within p6 domain) and a repeating Leu sequence $(LXX)_4$. (SEQ ID NO: 41). The $(LXX)_4$ (SEQ ID NO: 41) motif is a critical determinant for Vpr binding although it may not interact directly (see, e.g., Frankel, A. D. & Young, J. A., 1998, *Annu. Rev. Biochem.* 67, 1-25). The PTAPP (SEQ ID NO: 3) motif, or late (L) domain and, in particular, $Pro_{10,11}$, is the determinant of mature virus release during the final stages of assembly (Göttlinger, H. G., Dorfman, T., Sodroski, J. G. & Haseltine, W. A., 1991, *Proc. Natl. Acad Sci. USA* 88, 3195-3199; Huang, M., Orenstein, J. M., Martin, M. A. & Freed, E. O., 1995, *J. Virol.* 69, 6810-6818). The PTAPP (SEQ ID NO: 3) motif overlaps a region $(P_5XP_7,)$ that is critical for efficient packaging of pol gene products into the assembled virus particle (Dettenhofer, M. & Yu, X. F., 1999, *J. Virol.* 73, 4696-4704). The p6 region also contains Lys residues that are substrates for ubiquitination (Ott, D. E., Coren, L. V., Copeland, T. D., Kane, B. P., Johnson, D. G., Sowder, R. C., 2nd, Yoshinaka, Y., Oroszlan, S., Arthur, L. O. & Henderson, L. E., 1998, *J. Virol.* 72, 2962-2968). To determine whether any of the above conserved motifs were important for Tsg101 binding, deletion and point mutations were engineered into a plasmid encoding the p1-p6 region of Pr55$^{Gag}$ and protein-protein interactions were measured using the 2-hybrid assay. The p6 region from the pBH10 clone used for these studies contained 2 copies of the PTAPP (SEQ ID NO: 3) motif (Ratner, L., Haseltine, W., Patarca, R., Livak, K. 3., Starcich, B., Josephs, S. F., Doran, E. R., Rafalski, J. A., Whitehorn, E. A., Baumeister, K. & et al., 1985, *Nature* 313, 277-284) and each of these was deleted independently. Deletion of the first PTAPP (SEQ ID NO: 3) motif (aa 455-459, numbering within Gag) reduced β-galactosidase activity to a level that was ~50% that of wild-type protein binding (FIG. 1B). Deletion of the second PTAPP (SEQ ID NO: 3) motif (aa 467-471), which is conserved among all HIV strains and most lentiviruses (Myers, G., Korber, B., Wain-Hobson, S., Smith, R. F. & Pavlakis, G. N., 1995, Los Alamos National Laboratory, Los Alamos, N. Mex.), reduced β-galactosidase activity to ~25% that of wild-type protein binding. Deletion of both motifs (aa 455-459 and 467-471) reduced β-galactosidase activity to the level obtained when the vector lacked an insert (<0.3%). Deletion of the first PTAPP(SEQ ID NO: 3)-motif combined with substitution of Ala for $Pro_7$ in the second motif reduced enzyme activity to 25% that of wild-type. In the same context, substitution of Ala for $Pro_{10,11}$ blocked the interaction completely. Substitution of Arg for either or both of the Lys residues that serve as substrates for Ub modification (Ott, D. E., Coren, L. V., Copeland, T. D., Kane, B. P., Johnson, D. G., Sowder, R. C., 2nd, Yoshinaka, Y., Oroszlan, S., Arthur, L. O. & Henderson, L. E., 1998, *J. Virol.* 72, 2962-2968) gave wild-type β-galactosidase activity indicating that the Ub substrates in p6 are not required for Tsg101 recognition. Deletion of the $(LXX)_4$ (SEQ ID NO: 41) repeat motif reduced β-galactosidase activity to ~55% of the wild-type level. The same reduction was obtained when the first PTAPP (SEQ ID NO: 3) motif was removed in its entirety. The more deleterious impairment caused by deletion of the entire second highly conserved PTAPP (SEQ ID NO: 3) motif or by mutation of $Pro_{10,11}$, in this motif suggest that it is the major determinant of Tsg101 binding.

Tsg101 binds to Pr55$^{Gag}$ in vitro. To confirm and extend our observations with the 2-hybrid assay, in vitro co-immune precipitation studies were conducted using unlabeled bacteriophage T7 protein-tagged recombinant Pr55$^{Gag}$ expressed in bacteria (Ehrlich, L. S., Fong, S., Scarlata, S., Zybarth, G. & Carter, C., 1996, *Biochemistry* 35, 3933-3943.) and [$^{35}$S]-Met-labeled mouse or human Tsg101 expressed in RRL. Mouse (obtained from S. Cohen, Stanford U.) and human Tsg101 (from the B cell library) are 94% identical and were used interchangeably in these assays. The radiolabeled protein shown in FIG. 2A (lane 1) migrated at the molecular weight expected for Tsg101(391 amino acids, ~43 kDa). The protein was detected consistently as a doublet, perhaps due to internal initiation at $Met_{10}$. The protein was also sometimes detected as a doublet in cytoplasmic extracts. Tsg101 was captured by Protein A-coated beads on which antibodies directed against the T7 tag, CA, or p6 domains had been immobilized and pre-incubated with Pr55$^{Gag}$ (lanes 3, 7, 8, and 9). Beads not preincubated with Gag (lanes 2, 4, 5, 6) or preincubated with Gag in the absence of antibody did not capture Tsg101. The anti-p6 antibody recognizes an antigenic site in the C-terminal 16 residues of the protein (including the (Leu-X-X)$_4$ (SEQ ID NO: 41) repeat). The demonstration that the Pr55$^{Gag}$ bound to this anti-p6 antibody was still able to capture Tsg101 indicates that the Tsg101 binding region in p6 was exposed. This is consistent with the 2-hybrid assay result, which showed that the C-terminal half of the p6 region was not a Tsg101 binding site. In competition assays, addition of a 5-fold molar excess of a peptide containing the PTAPP (SEQ ID NO: 3) motif (ALQSRPEPTAPPEES) (SEQ ID NO: 4) caused a 2.2-fold reduction in Tsg101 capture by Pr55$^{Gag}$. The limited solubility of the peptide precluded testing at higher concentrations. In contrast, no change was detected with a 5-fold molar excess of a peptide containing the mutant LIAPP (SEQ ID NO: 43) sequence, indicating that the effect of the PTAPP (SEQ ID NO: 3) motif was specific. Western analysis with an anti-CA monoclonal antibody confirmed the presence of full-length Pr55$^{Gag}$ on the beads coated with the anti-T7, -CA and -p6 antibodies that captured Tsg101 (FIG. 2B, lanes I-4). The results of the immune capture assay demonstrate that Tsg101 interacts specifically and stably with Pr55$^{Gag}$ in vitro through interaction with the L domain.

Tsg101 binds $Pr_{55}^{Gag}$ in vivo. To determine if Tsg101 and Gag associate during viral assembly, COS cells expressing Gag were examined for Tsg101-Gag complexes by co-immune precipitation assays. Plasmid pgp-RRE-r expresses the HIV-1 Gag and Gag-Pol polyproteins as well as Vif under the control of the SV40 late promoter (Smith, A. J., Cho, M. I., Hammarskjold, M. L. & Rekosh, D., 1990, *J. Virol.* 64, 2743-2750). Expression requires the Rev protein, which is provided in trans by expression of pCMV-rev (Smith, A. J., Cho, M. I., Hammarskjold, M. L. & Rekosh, D., 1990, *J. Virol.* 64, 2743-2750). To ensure the specificity of the Tsg101-Gag interaction in the cytoplasm, a Gag mutant that lacked the p6 domain was included. Cytoplasmic extracts prepared from cells transfected with rev alone, rev, gag, and pol, or rev, gagΔp6, and pol were incubated with anti-Tsg101 mouse monoclonal antibody and the immune-precipitate was examined for Gag-related proteins by Western blotting with a goat polyclonal antibody against the NC domain. First, the total cytoplasmic extract was examined (FIG. 3A). The anti-NC antibody recognized Pr55$^{Gag}$, an 18 kDa NC-related protein, and NCp7 in the extract prepared from cells expressing the wild-type Gag protein (lane 2). The 18 kDa band was identified as NC-p6 based on its reactivity with both anti-NC and anti-p6. The anti-NC antibody also recognized NCp7 and a protein that migrated at ~49 kDa in the extract prepared from cells expressing the mutant (lane 3). The latter is the molecular weight expected for the Pr55$^{Gag\Delta p6}$ precursor protein. Consistent with this conclusion, the 49 kDa protein was not detected in extracts prepared from cells expressing Rev alone (lane 1) or the wild-type Gag protein (lane 2). Immune-precipitation using a monoclonal antibody against Tsg101 precipitated the wild-type Gag precursor and the NC-p6 protein, but not NCp7 (FIG. 3B, lane 2) or Gag lacking the p6 domain (lane 3). Re-probing the same blot with another anti-Tsg101 antibody confirmed the presence of the cellular protein in the immune-precipitates of all three extracts (lanes 4-6). In a reciprocal experiment, anti-CA antibody co-immune-precipitated Tsg101 from extracts of cells expressing Gag (FIG. 3C, lane 2) but not extracts expressing Rev alone (lane 1). Re-probing the same blot with another anti-CA antibody confirmed the presence of Gag on the beads that captured Tsg101 (lane 4). Immune precipitation with an irrelevant antibody (rabbit anti-mouse IgG) did not precipitate Gag or Tsg101. The results indicate that the interaction between Tsg101 and Gag occurs in the cytoplasm of cells containing the viral protein and demonstrate that the p6 region of the Gag protein specifically directs the interaction.

Identification of the region in Tsg101 that interacts with Pr55$^{Gag}$. The Tsg101 protein contains an N-terminal E2-like (UEV) domain with homology to the Ub-conjugating (Ubc) 4 subgroup of E2 enzymes (Koonin, E. V. & Abagyan, R. A., 1997, *Nat. Genet.* 16,330-331; Ponting, C. P., Cai, Y.-D. & Bork, P., 1997, *J. Mol. Med.* 75,467-469). It also contains central Pro-rich and coiled-coil regions, and a C-terminal steadiness box (SB) that controls its steady state level (FIG. 4; Feng, G. H., Lih, C. J. & Cohen, S. N., 2000, *Cancer Res.* 60, 1736-1741). Based on recent findings implicating Ub in Gag assembly (Ott, D. E., Coren, L. V., Copeland, T. D., Kane, B. P., Johnson, D. G., Sowder, R. C., 2nd, Yoshinaka, Y., Oroszlan, S., Arthur, L. O. & Henderson, L. E., 1998, *J. Virol.* 72,2962-2968; Schubert, U., Ott, D. E., Chertova, E. N., Welker, R., Tessmer, U., Princiotta, M. F., Bennink, J. R., Krausslich, H. G. & Yewdell, J. W., 2000, *Proc. Natl. Acad. Sci. USA* 97, 13057-13062; Strack, B., Calistri, A., Accola, M. A., Palu, G. & Gottlinger, H. G., 2000, *Proc. Natl. Acad. Sci. USA* 97, 13063-13068; Vogt, V. M., 2000, *Proc. Natl. Acad Sci. USA* 97, 12945-12947; Ott, D. E., Coren, L. V., Chertova, E. N., Gagliardi, T. D. & Schubert, U., 2000, *Virology* 278, 111-121; Patnaik, A., Chau, V. & Wills, J. W., 2000, *Proc. Natl. Acad. Sci. USA* 97, 13069-13074), it was of interest to determine which region of Tsg101 was recognized by the viral protein. To investigate this, the yeast 2-hybrid system was used to localize the region in Tsg101 required for interaction with Pr55$^{Gag}$. Plasmids encoding N- or C-terminally-truncated Tsg101 fused to the activation domain of the GAL4 protein were assayed for the ability to bind p1-p6 fused to the GAL4 DNA-binding domain. As shown in FIG. 4A, assessment of reporter gene activation indicated that p6-Tsg101 interaction was maintained in fragments that retained the N-terminal 155 amino acids, but lost in the mutants that lacked this region, suggesting that the N-terminal region was the minimal determinant of binding. Western analysis showed comparable expression of the interacting and non-interacting fragments, thus supporting this conclusion. Curiously, the N-terminal 155-, 215-, and 311-residue fragments bound p6 comparably in a qualitative assay, but the 311-residue fragment interacted to a significantly greater extent in the quantitative assay (FIG. 4A). This difference did not reflect a binding site downstream of aa155 since a fragment extending from aa139 to the C-terminus of Tsg101 failed to interact. Moreover, no binding was detected in in vitro capture assays using a hybrid protein comprised of GST fused to Tsg101 residues 167-374. Optimal presentation of the p6 binding region in the N-terminal 155 residue fragment may require downstream sequences. In this regard, Tsg101 resembles class II E2 enzymes with a conserved catalytic core domain of ~150 residues and an extra C-terminal extension attached to this core domain that is speculated to play a role in substrate recognition (Jentsch, S., Seufert, W., Sommer, T. & Reins, H. A., 1990, Trends Biochem. Sd. 15, 195-198; Li, L. Liao, J., Ruland, J., Mak, T. W. & Cohen, S. N., 2001, *Proc. Natl. Acad. Sci. USA* 98, 1619-1624).

In E2 enzymes including Ubc4, Ub is conjugated to an active site Cys. In Tsg101, Tyr replaces this Cys residue. However, 8 of 14 residues flanking this Tyr are conserved in both Tsg101 and Ubc4 (Koonin, E. V. & Abagyan, R. A., 1997, *Nat. Genet.* 16,330-331; Ponting, C. P., Cai, Y.-D. & Bork, P., 1997, *J. Mol. Med.* 75,467-469; FIG. 4B). To determine whether recognition by the p6 domain was due to amino acids unique to Tsg101, point mutations were engineered into the active site homologue in the full-length protein and interaction with p6 was tested in the 2-hybrid assay. Western analysis using an antibody against the GAD moiety in the fusion proteins showed that the mutated and wild-type proteins were all expressed at comparable levels. Mutation of Trp$_{117}$, which is conserved in all classes of E2 and UEV proteins and believed to demarcate the C-terminus of the active site region (Koonin, E. V. & Abagyan, R. A., 1997, *Nat. Genet.* 16,330-331; Hershko, A. & Ciechanover, A., 1998, *Annu. Rev. Biochem.* 67,425-479) eliminated binding completely, indicating that this residue is important in both Tsg101 and Ubc4. Consistent with the hypothesis that residues unique to Tsg101 determined L domain interaction, substitution of 3 of the 4 non-conserved residues tested impaired p6 binding (FIG. 4B). Conservative substitution of Trp for Tyr$_{110}$ reduced p6 interaction to 31% of wild-type. Substitution of the hydrophobic amino acid Val for Tyr$_{113}$ reduced binding to 33% of wild-type. Substitution of Ala for Lys$_{118}$ reduced binding to a lesser extent.

To further test the hypothesis, we examined residues in Tsg101 that are not conserved in E2 enzymes, but align with regions previously shown to determine substrate recognition in the Ubc4 subgroup (Koonin, E. V. & Abagyan, R. A., 1997, *Nat. Genet.* 16,330-331; Ponting, C. P., Cai, Y.-D. & Bork, P., 1997, *J. Mol. Med.* 75,467-469; Oughtred, R., Bedard, N, Vrielink, A. & Wing, S. S., 1998, *J. Biol. Chem.* 273, 18435-18442). Residues 49 and 125 in Ubc4 were found to determine the substrate specificity of structurally homologous, but functionally distinct Ubc4 isoforms (Oughtred, R., Bedard, N, Vrielink, A. & Wing, S. S., 1998, *J. Biol. Chem.* 273, 18435-18442). Residue 49 aligns with Tsg101 Thr$_{67}$ (Koonin, E. V. & Abagyan, R. A., 1997, *Nat. Genet.* 16,330-331; Sancho, E. Vila, M. R., Sanchez-Pulido, L., Lozano, 3.3., Paciucci, R., Nadal, M., Fox, M., Harvey, C. Bercovich, B., Loukili, N., Ciechanover, A., Lin, S. L., Sanz, F. Estivill, X., Valencia, A. & Thomson, T. M., 1998, *Mol. Cell Biol.* 18, 576-589) or Asn$_{69}$ (Ponting, C. P., Cai, Y.-D. & Bork, P., 1997, *J. Mol. Med.* 75,467-469). Residue 125 aligns with Ser$_{149}$ (24) or Tyr$_{150}$ (Sancho, E. Vila, M. R., Sanchez-Pulido, L., Lozano, 3.3., Paciucci, R., Nadal, M., Fox, M., Harvey, C. Bercovich, B., Loukili, N., Ciechanover, A., Lin, S. L., Sanz, F. Estivill, X., Valencia, A. & Thomson, T. M., 1998, *Mol. Cell Biol.* 18, 576-589). We therefore substituted Ala for $_{69}$Thr- Tyr-Asn$_{69}$ and $_{149}$Ser-Tyr$_{150}$ and determined the effect on binding. As shown in FIG. 4C, mutation of $_{69}$Thr-Tyr-Asn$_{69}$ reduced binding to 5% of the wild-type level. Mutation of $_{149}$Ser-Tyr$_{150}$ had no effect. Western blotting confirmed that the mutants were expressed at wild-type levels. The results are consistent with the conclusion that the interaction of Gag with Tsg101 is based on specific recognition and support the suggestion that the N-terminal E2-like domain of Tsg101 is the minimal determinant of p6 binding.

Discussion

In this example, the interaction of Tsg101 with HIV-1 Pr55$^{Gag}$ in vitro and in vivo is described. The N-terminal half of Tsg101, which contains the determinant of Gag binding, is homologous to Ub-conjugating E2 enzymes (Koonin, E. V. & Abagyan, R. A., 1997, *Nat. Genet.* 16,330-331; Ponting, C. P., Cai, Y.-D. & Bork, P., 1997, *J. Mol. Med.* 75,467-469; Jentsch, S., Seufert, W., Sommer, T. & Reins, H. A., 1990, *Trends Biochem. Sd.* 15, 195-198). The C-terminal half of Tsg101 has a coiled-coil domain that can interact with a cytoplasmic phosphoprotein, stathmin, implicated in microtubule dynamics (Li, L. & Cohen, S. N., 1996, *Cell* 85, 319-329), and contains a highly conserved sequence that regulates the steady state level of the protein (Smith, A. J., Cho, M. I., Hammarskjold, M. L. & Rekosh, D., 1990, *J. Virol.* 64, 2743-2750). Based on its structural features, Tsg101 has been speculated to be (i) a dominant-negative Ub regulator (Koonin, E. V. & Abagyan, R. A., 1997, *Nat. Genet.* 16,330-331; Ponting, C. P., Cai, Y.-D. & Bork, P., 1997, *J. Mol. Med.* 75,467-469); (ii), a transcriptional regulator (Sun, Z., Pan, 3., Hope, W. X., Cohen, S. N. & Balk, S. P., 1999, *Cancer* 86,689-96); (iii), a regulator of the cell cycle (Xie, W., Li, L. & Cohen, S. N., 1998, *Proc. Natl. Acad. Sci. USA* 95, 1595-1600; Zhong, Q., Chen, Y., Jones, D. & Lee, W. H., 1998, *Cancer Res.* 58,2699-2702); and (iv), a regulator of membrane protein trafficking (Babst, M., Odorizzi, G., Estepa, E. J. & Emr, S. D., 2000, *Traffic* 1,242-258; Lemmon, S. K. & Traub, L. M., 2000, *Curr. Opin Cell Biol.* 12,457-466). It is not clear whether these apparently diverse roles reflect independent or related functions of the protein. Furthermore, how participation in these functions may relate to Tsg101's role in the ubiquitination process is unknown.

The observation that Tsg101 interacts with HIV-1 Gag in mammalian cells suggests that the interaction is relevant to the viral life cycle. It is noted that the interaction was much more efficient in cytoplasmic extracts than in vitro, perhaps suggesting a need for stabilizing cellular factors or a particular Gag assembly state. The fact that the L domain-containing p6 region of the protein is required for binding implicates the interaction in the late budding function. The results described in this example indicate that deletion of the L domain PTAPP (SEQ ID NO: 3) motif prevents the interaction of Gag with Tsg101. This Pro-rich sequence is highly conserved in all lentiviruses except equine infectious anemia virus (Myers, G., Korber, B., Wain-Hobson, S., Smith, R. F. & Pavlakis, G. N., 1995, Los Alamos National Laboratory, Los Alamos, N. Mex.). It is duplicated in some isolates of HIV-1, HIV-2 and simian immunodeficiency virus (SIV). The human T-cell leukemia virus type 1 (HTLV-1) and the Mason-Pfizer monkey virus (MPMV) Gag proteins contain both the lentivirus motif (PT(S)AP) and the (P)PPPY (SEQ ID NO: 44) motif, the functionally interchangeable avian retrovirus counterpart (Wills, J. W., Cameron, C. E., Wilson, C. B., Xiang, Y., Bennett, R. P. & Leis, J., 1994, *J. Virol.* 68,6605-6618; Parent, L. J., Bennett, R. P., Craven, R. C., Nelle, T. D., Krishna, N. K., Bowzard, J. B., Wilson, C. B., Puffer, B. A., Montelaro, R. C. & Wills, J. W., 1995, *J. Virol.* 69, 5455-5460). Studies indicating that the PY and PTAP (SEQ ID NO: 39) motifs recruit the Ub machinery and that certain proteasome inhibitors cause alterations in viral particle budding similar to defects resulting from mutations in PTAPP (SEQ ID NO: 3) and PY support the possibility that the cell's ubiquitination machinery is linked to viral assembly (Schubert, U., Ott, D. E., Chertova, E. N., Welker, R., Tessmer, U., Princiotta, M. F., Bennink, J. R., Krausslich, H. G. & Yewdell, J. W., 2000, *Proc. Natl. Acad Sci. USA* 97, 13057-13062; Strack, B., Calistri, A., Accola, M. A., Palu, G. & Gottlinger, H. G., 2000, *Proc. Natl Acad. Sci. USA* 97, 13063-13068; Patnaik, A., Chau, V. & Wills, J. W., 2000, *Proc. Natl. Acad. Sci. USA* 97, 13069-13074). However, it is unclear at this time whether this link reflects a direct or indirect involvement of Ub: On one hand, mutation of the Lys residues in the p6 domain that are substrates for Ub modification has no apparent effect on virus assembly or release (Ott, D. E., Coren, L. V., Chertova, E. N., Gagliardi, T. D. & Schubert, U., 2000, *Virology* 278, 111-121). On the other hand, covalent linkage of Ub to Gag was shown to rescue the defect in release caused by proteasome inhibitors (Patnaik, A., Chau, V. & Wills, J. W., 2000, *Proc. Natl. Acad. Sci. USA* 97, 13069-13074). Perhaps other Lys residues serve as Ub substrates when the preferred sites in p6 are not available.

The notion that Tsg101 functions as a dominant-negative Ub regulator is based on the fact that Tsg101 lacks the active site Cys residue that conjugates Ub in active E2 enzymes (Koonin, E. V. & Abagyan, R. A., 1997, *Nat. Genet.* 16,330-331; Ponting, C. P., Cai, Y.-D. & Bork, P., 1997, *J. Mol. Med.* 75,467-469). The ubiquitination process requires the sequential action of two or three enzymes (see, e.g., Hershko, A. & Ciechanover, A., 1998, *Annu. Rev. Biochem.* 67, 425-479). E1, an Ub-activating enzyme, binds Ub through a thioester bond, then transfers it to E2. E2 enzymes can function alone or in conjunction with E3 Ub-protein ligases to attach Ub to lysine residues in substrate proteins. Substrates modified by polyubiquitination are degraded by the proteasome; monoubiquitination serves as a signal for endocytosis (Shili, S. C., Sloper-Mould, K. E. & Hicke, L., 2000, *EMBO. J.* 19, 187-198). Although the active site Cys is not conserved in Tsg101, our results suggest that this region functions directly or indirectly in binding of the HIV-1 L domain. It is noteworthy that the residues in the altered Ub-binding site in Tsg101 that contribute to L domain PTAPP (SEQ ID NO: 3) binding are Tyr and Trp residues flanked by positively charged Lys residues (FIG. 4B). Aromatic amino acids flanked by charged residues are critical binding determinants for protein binding motifs like SH3 and WW domains. SH3 domains bind Pro-rich sequences having the consensus PXXP, like PTAPP(SEQ ID NO: 3); WW domains interact with PPXY motifs (Kay, B. K., Williamson, M. P. & Sudol, M., 2000, FASEBJ. 14, 231-241; Gamier, L., Wills, J. W., Verderame, M. F. & Sudol, M., 1996, *Nature* 381, 744-745). Moreover, as the amino acids surrounding these aromatic residues in Tsg101 are conserved in active E2 enzymes, Tsg101 may maintain an E2-like ability to present Gagp6 to interacting E3 enzymes, as suggested for E2-Ub-E3 interacting complexes (Laney, J. D. & Hochstrasser, M., 1999, *Cell* 97, 427-430; Nuber, U. & Schefflier, M., 1999, *J. Biol. Chem.* 274, 7576-7582). If so, the Tsg101-Gag-complex may associate with an active E3 enzyme to facilitate an event related to L domain function. Furthermore, Tsg101 has been shown to function in membrane protein transport (Babst, M., Odorizzi, G., Estepa, E. J. & Emr, S. D., 2000, *Traffic* 1, 242-258; Lemmon, S. K. & Traub, L. M., 2000, *Curr. Opin Cell Biol.* 12,457-466). Its involvement in regulation of vesicles that are required for recycling of membrane-associated proteins (Babst, M., Odorizzi, G., Estepa, E.

J. & Emr, S. D., 2000, *Traffic* 1, 242-258; Bishop N and Woodman P., 2001, *J Biol Chem*. 276:11735-42) may permit it to play a role in Gag trafficking to the site of particle maturation and release.

The finding that HIV-1 Gag binds through the E2-like domain in Tsg101 suggests several hypotheses. The interaction of Gag with Tsg101 may be adventitious, based on Tsg101's similarity to active E2 enzymes. Alternatively, if Ub is required for assembly as suggested (Schubert, U., Ott, D. E., Chertova, E. N., Welker, R., Tessmer, U., Princiotta, M. F., Bennink, J. R., Krausslich, H. G. & Yewdell, J. W., 2000, *Proc. Natl. Acad. Sci. USA* 97, 13057-13062; Strack, B., Calistri, A., Accola, M. A., Palu, G. & Gottlinger, H. G., 2000, *Proc. Natl. Acad. Sci. USA* 97, 13063-13068; Patnaik, A., Chau, V. & Wills, 3. W., 2000, *Proc. Natl. Acad. Sci. USA* 97, 13069-13074), Tsg101 may function as a cellular defense mechanism that prevents Gag interaction with active E2 enzymes. It is also possible that Tsg101 is recruited by the virus as a chaperone to block Gag polyubiquitination and subsequent degradation by the proteasome. This idea is supported by the fact that cyclin-specific E2 enzymes with Ser substituted for the active Cys are, in fact, dominant negative inhibitors of cyclin destruction (Townsley, F. M., Aristarkhov, A., Beck, S., Hershko, A. & Ruderman, J. V., 1997, *Proc. Natl. Acad. Sci USA* 94,2362-2367). Finally, Tsg101 may function like the yeast UEV Mms2 protein, which alters the function of interacting E3 proteins (Hofmann, R. M. & Pickart, C. M., 1999, *Cell* 96, 645-653). Interestingly, the L domain of the Ebola virus matrix protein interacts with Nedd4, an E3 Ub protein ligase (Harty, R. N., Brown, M. E., Wang, G., Huibregtse, J. & Hayes, F. P., 2000, *Proc. Natl. Acad Sci. USA* 97, 13871-13876). The apparent conservation of L domain interaction with cellular proteins that affect Ub modification suggests that the involvement of the Ub machinery is a highly conserved event in virus assembly and particle release both within and outside the retrovirus family.

6.2. Example 2

Example 1 demonstrates that the PTAPP (SEQ ID NO: 3) motif or L domain of human immunodeficiency virus type 1 (HIV-1), which is located in the C-terminal p6 region of the Gag precursor polyprotein, was found to bind to the protein product of the tsg101 gene. Sequence analysis has suggested, and experimental evidence has shown, that Tsg101 can function in both the modulation of transcription and the inhibition of ubiquitination and protein decay. The latter effects are mediated by an N-terminal region that contains a ubiquitin (Ub) conjugase (E2)-like domain, but lacks an active site Cys residue crucial to Ub conjugation. This domain of Tsg101 is the minimal binding region required for its interaction with HIV-1 Gag. The involvement of Tsg101 in endosomal trafficking, together with its ability to interact with HIV-1 Gag in vitro and in mammalian cells as shown in example 1, and the finding that the L domain in the p6 region of Gag is specifically required for binding, have led to studies in this example to investigate the effects of Tsg101 on the late budding function responsible for mature virus release from the cell surface.

In this example, it is shown that the release of mature HIV-1 particles is reduced in murine SL6 cells, which are deficient in Tsg101 (Li, L. & Cohen, S. N., 1996, *Cell* 85, 319-329), as well as in primate COS-1 cells that overproduce the wild-type Tsg101 protein. It has also been shown that SL6 cells are defective in sorting of multiple surface-bound proteins (Babst, M., Odorizzi, G., Estepa, E. J. & Emr, S. D., 2000, *Traffic* 1, 242-258). Mutation of Tsg101 in a region necessary for regulation of Tsg101 protein decay, but not for Gag binding (see Example 1), partially reversed the inhibitory effects of Tsg101 over-expression on virus release. The effects of Tsg101 overproduction required the presence in Gag of sequences that interact with Tsg101. The results in this example provide evidence that the Tsg101 protein specifically regulates the transport and maturation of HIV-1 particles through its interaction with the L domain of Gag, implicating Tsg101 function in productive virus assembly.

The p6 region in Pr55$^{Gag}$, the structural precursor polyprotein encoded by human immunodeficiency virus type I (HIV-1), directs release of mature virus-like particles from the plasma membrane of gag-transfected cells. Example 1 demonstrates that Gag$^{p6}$ binds to Tsg101, a protein that affects trafficking of membrane-associated proteins. In this example, it is demonstrated that Tsg101 deficiency induced by functional inactivation of Tsg101 mRNA by an antisense transcript prevented Gag protein maturation in a cellular fraction enriched in plasma membranes and reduced virus particle release, suggesting that Tsg101 is required for normal Gag trafficking and processing. Paradoxically, overexpression of Tsg101 also inhibited the release of virus particles but did not affect exit of GagΔp6, which does not bind Tsg101. Inhibition was reduced by mutation of the Tsg101 C-terminal steadiness box (SB) domain, which is required for proper autoregulation of Tsg101 decay. However, while the SB mutation decreased the ability of overexpressed Tsg101 to interfere with virus particle release, maturation of the particle-associated Gag precursor protein was defective. The results in this example suggest that Tsg101 has a role in both the maturation and release of HIV particles, potentially providing a novel target for interfering with HIV-1 production.

Materials And Methods

Plasmids. pgp-RRE-r (Smith, A. J., Cho, M. I., Hammarskjold, M. L. & Rekosh, D., 1990, *J. Virol*. 64, 2743-2750), encoding wild-type gag, pol, and vif was used as a template to synthesize Pr55 GagΔp6 by engineering three point mutations in the first codon of p6 by PCR, converting it to a stop (ochre) codon. The 5' primer (GGAAGATCTGGCCTTC-CTACAAGGGAAGGCCAGGGAATT, SEQ ID NO:37) anneals to nt 1637 to 1687 of BH10 gag (Ratner, L., Haseltine, W., Patarca, R., Livak, K. J., Starcich, B., Josephs, S. F., Doran, E. R., Rafalski, J. A., Whitehorn, E. A., Baumeister, K. & et al., 1985, *Nature* 313, 277-284) and includes a unique BglII site. The 3' primer (CCATGTATTGATAGATAACTAT-GTCTG, SEQ ID NO:38) anneals to nt 2655 to 2682 in the pol gene downstream of a unique EcoRV site. The pgp-RRE-r plasmid and the fragment produced from PCR were cut with BglII and EcoRV and the desired fragments were ligated. The mutation was confirmed by sequencing with ABI Prism Big-Dye Terminator Cycle Sequencing Ready Reaction kit (Perkin-Elmer, Foster City, Calif.). pIND-hTsg101-FLAG (wild-type human Tsg101) and pIND-SD5-59-FLAG, in which Gly replaces amino acids 348-351, are described (Feng, G. H., Lih, C.-J., & Cohen, S. N., 2000, *Cancer Research* 60, 1736-1741).

Cell culture, transfection, and preparation of cytoplasmic extracts. COS-1 cells were cultured in DMEM supplemented with fetal bovine serum and antibiotics to 60% confluency at 37° C. The cells were transfected with wild-type or mutated pIND-hTsg101-FLAG, pVgRXR, pCMV-rev, and wild-type or mutated pgp-RRE-r in various combinations using the FuGene 6 reagent (Roche). Rev is a HIV-1-encoded protein required for expression of gag and pol (Frankel, A. D. & Young, J. A., 1998, *Annu. Rev. Biochem*. 67, 1-25). PVgRXR encodes both monomers of a heterodimeric ecdysone-inducible receptor that, together with the hormone, form a transcriptional activator complex that binds the promoter driving tsg101 expression. Treating the transfected cells with the ecdysone analogue, pronasterone, for 24 hr at 24 hr after transfection induced expression of Tsg101. At 48 hr post-transfection, the cells were harvested by scraping into the media and collected by centrifugation. The pelleted cells were washed three times with cold PBS, swollen in 1 ml of cold hypotonic buffer (10 mM Tris, pH 7.4, 1 mM $MgCl_2$) containing protease inhibitors (15 min, 4° C.) and disrupted with 35 strokes of a Dounce homogenizer (type B pestle). The lysate was spun 10 min, 1,000×g at 4° C. to remove unbroken cells, nuclei, and mitochondria. NIH 3T3 and SL6 cells were maintained at 37° C. in DMEM supplemented with antibiotics and fetal bovine serum. SL6 cells are 3T3 derivatives that have undergone functional inactivation of the tsg101 gene by antisense RNA using a previously described random homozygous knockout (RHKO) procedure (Li, L. & Cohen, S. N., 1996, Cell 85, 319-329). These cells were transfected with pHIV-APΔenv (Sutton, R. E., Wu, H. T., Rigg, R., Bohnlein, E. & Brown, P. O., 1998, J. Virol. 72, 5781-5788) and, where indicated in the text, with pME VSV G (Sutton, R. E., Wu, H. T., Rigg, R., Bohnlein, E. & Brown, P. O., 1998, J. Virol. 72, 5781-5788) using the FuGene 6 reagent. Fractionation into total cytoplasm (S1), nuclei/Golgi-enriched (P1), soluble (S100) and plasma membrane-enriched (P100) fractions was performed as described (L. Alland, S. M. Peseckis, R. E. Atherton, L. Berthiaume & Resh, M. D., 1994, J. Biol. Chem. 269, 16701-16705). Virus particles were isolated from culture supernatant passed through a 0.45 μm filter by ultracentrifugation through a cushion of 20% sucrose at 30,000 rpm for 80 min at 4° C. (Beckman SW41 rotor). The pelleted viral particles were resuspended in 1 ml of phosphate buffered saline by gentle shaking at 4° C. Infectivity of VSV G pseudotyped virus preparations was assessed using the MAGI assay (Vodicka, M. A., Goh, W. C., Wu, L. I., Rogel, M. E., Bartz, S. R., Schweickart, V. L., Raport, C., & Emerman, M., 1997, Virol. 233, 193-198).

Immunoprecipitation assay. Protein A agarose beads (Pierce), pre-washed with non-denaturing hypotonic (10 mM Tris, pH 7.4, 1 mM $MgCl_2$) buffer containing protease inhibitors (Roche), were incubated with the appropriate antibody, added to cytosolic extracts and rotated at 4° C. for 60 min. Immunoprecipitates were washed in hypotonic buffer, boiled in SDS sample buffer with 5% mercaptoethanol, resolved by SDS-PAGE and analyzed by Western blotting with the antibodies indicated in the text.

Protein detection. Proteins were separated by electrophoresis through 12.5% SDS-polyacrylamide gels. Following electrophoresis, the gels were transferred to nitrocellulose and analyzed by Western blotting. The following antibodies were used, as specified in the text: anti-Tsg101 mouse monoclonal antibody (Santa Cruz, Inc); anti-Tsg101 rabbit polyclonal antipeptide antibody raised against amino acids 383-391; anti-FLAG mouse monoclonal (obtained from Sigma); anti-CA rabbit polyclonal antibody raised against a native form of the CA protein (Ehrlich, L. S., Krausslich, H.-G., Wimmer, E. & Carter, C. A., 1990, AIDS & Hum. Retro. 6, 1169-1175.); anti-CA mouse monoclonal antibody (NEN-DuPont); anti-p6 rat monoclonal antibody (ABI). Proteins were visualized by chemiluminescence using Lumi-Light reagents (Roche).

Results

Effect of Tsg101 deficiency on virus production. Example 1 has demonstrated that Tsg101 associates specifically with the L domain in HIV-1 Pr55 $Gag^{p6}$, a region that directs exocytosis of mature viral particles from infected cells (Göttlinger, H. G., Dorfman, T., Sodroski, J. G. & Haseltine, W. A., 1991, Proc. Natl. Acad Sci. USA 88, 3195-3199; Huang, M., Orenstein, J. M., Martin, M. A. & Freed, E. O., 1995, J. Virol. 69, 6810-6818). To investigate the role of this interaction in viral production, the effect of modulating tsg101 expression on viral particle release was determined. As an initial approach, virus production was examined in a NIH 3T3-derived cell line (SL6) in which Tsg101 expression has been reduced to 30% of normal levels using an antisense strategy (Li, L. & Cohen, S. N., 1996, Cell 85, 319-329).

For these experiments, Gag and all of the other viral proteins except Nef and Env were expressed from pHIV-APΔenv (Sutton, R. E., Wu, H. T., Rigg, R., Bohnlein, E. & Brown, P. O., 1998, J. Virol. 72, 5781-5788) and the virus particles released into the media were assessed by Western blotting. pHIV-APΔenv contains the human placental alkaline phosphatase gene in place of the nef gene and the env gene has been deleted. Growth conditions were identified to obtain cell cultures matched for extent of confluency as measured by total protein staining and Western blot analysis of specific subcellular compartment markers. In control experiments, it is ascertained that SL6 was transfected as efficiently as 3T3 using the Fugene6 reagent. Cytoplasmic (S1) extracts prepared from matched cultures of transfected parental and mutant cells and exhibiting total protein values within +/−0.01 μg of each other showed identical Coomassie blue stained protein patterns (FIG. 5A, lanes 1, 2) and comparable expression of $Na^+K^+$ATPase and actin (lanes 3,4). In contrast, as previously reported, SL6 cells accumulated Tsg101 at ~30% the level of the parental cells, as determined by comparative semi-quantitative Western analysis using an anti-Tsg101 monoclonal.

Analysis of cell-associated Gag protein in 3T3 and SL6 cells. To determine the effect of Tsg101 deficiency on the intracellular accumulation of Gag, the transfected cells were subjected to differential centrifugation and the amount of viral protein was assessed in the S1 lysate and in subcellular fractions. The S1 lysate prepared from transfected 3T3 cells, but not mock-treated cells, contained mature CA protein (FIG. 5C, lanes 1, 2), which accumulated in the plasma membrane-enriched P100 fraction (inset to FIG. 5C). This fraction was identified by localization of $Na^+K^+$ATPase, an integral plasma membrane protein (see, e.g., L. Alland, S. M. Peseckis, R. E. Atherton, L. Berthiaume & Resh, M. D., 1994, J. Biol. Chem. 269, 16701-16705). In contrast, no mature CA was detected in the S1 fractions prepared from mock-treated or transfected SL6 cells (FIG. 5C, lanes 3, 4). Further analysis of the S1 and P1 fractions from the SL6 cells using an antibody that recognizes the Gag precursor confirmed the absence of virus-specific protein in the S1 fractions prepared from these untreated or transfected SL6 cells (FIG. 5D, lanes 1,2). In contrast, the antibody revealed the full-length Gag precursor in the P1 fraction (lane 4), which is enriched in filamentous actin-, Golgi complex-, and nuclear proteins (see, e.g., L. Alland, S. M. Peseckis, R. E. Atherton, L. Berthiaume & Resh, M. D., 1994, J. Biol. Chem. 269, 16701-16705). These results suggest that the block to virus release in SL6 cells resulted from defective transport of the Gag precursor to the plasma membrane where it normally assembles, and consequently implicate Tsg101 in this transport function.

Effect of Tsg101 overproduction on release of HIV-1 particles. The steady-state level of Tsg101 protein is maintained within a narrow range during cell growth by a post-translational mechanism involving protein degradation (Feng, G. H., Lih, C.-J., & Cohen, S. N., 2000, Cancer Research 60, 1736-1741). Overexpression of a FLAG-tagged Tsg101 protein leads to accelerated turnover of both the endogenous and FLAG-tagged protein (Feng, G. H., Lih, C.-J., & Cohen, S. N., 2000, *Cancer Research* 60, 1736-1741). Use of a pIND-h-Tsg101-FLAG construct (Feng, G. H., Lih, C.-J., & Cohen, S. N., 2000, *Cancer Research* 60, 1736-1741) enables inducible expression of FLAG-tagged Tsg101 under control of a modified promoter containing Drosophilia ecdysone-responsive DNA elements. In preliminary experiments using the ecdysone analog, pronasterone inducer (hereinafter "pa"), the conditions that allowed to overproduce FLAG-tagged Tsg101 without drastic perturbation of the steady-state level of endogenous protein was identified. As shown in FIG. 6A, Western analysis using anti-Tsg101 antibody detected an endogenous protein band migrating at the expected ~46 kDa position and increasing amounts of a protein that migrated more slowly. Re-probing the blot with antibody against the eight residue FLAG sequence confirmed that the more slowly migrating protein was FLAG-tagged Tsg101 derived from expression of the induced plasmid encoding the protein.

As previously demonstrated, plasmid pgp-RRE-r, when co-expressed in COS cells with the HIV-1 regulatory protein, Rev, allows assembly and release of virus-like particles that are indistinguishable from mature HIV-1 (Smith, A. J., Cho, M. I., Hammarskjold, M. L. & Rekosh, D., 1990, *J. Virol.* 64, 2743-2750, Ebbets-Reed, D., Scarlata, S. & Carter, C. A. *Biochem.* 35, 14268-14275). To ensure the specificity of any Tsg101-related effects we observed, the HIV-1 GagΔp6 mutant was examined in parallel. The mutated Gag protein (i) lacks the p6 domain that binds Tsg101; (ii) assembles particles that fail to complete proteolytic maturation; and (iii) is released inefficiently (see, Example 1; Göttlinger, H. G., Dorfman, T., Sodroski, J. G. & Haseltine, W. A., 1991, *Proc. Natl. Acad Sci. USA* 88, 3195-3199; Huang, M., Orenstein, J. M., Martin, M. A. & Freed, E. O., 1995, *J. Virol.* 69, 6810-6818). It was found that particles containing GagΔp6 are released at 50% wild-type efficiency, as measured by comparing accumulation in the cytoplasm and media. The effect of increasing amounts of Tsg101 on release of virus particles was determined by adding the pa inducer at 0, 1, and 5 μM to cells transfected with a constant amount of pIND-h-Tsg101-FLAG DNA, rev, pol and gag or gagΔ6 and examining the culture media for virus-like particles. As expected, no virus-specific protein was released from cells expressing only rev (FIG. 6B, lane 1). Viral particles released from cells treated with 0 μM pa contained the expected band of mature CA protein (lane 2). The virus released from cells treated with 1 or 5 μM pa exhibited the same mature CA composition, but the amount was reduced to ~60% and ~30%, respectively, of the control (0 μM pa) level (lanes 3 and 4, respectively). Addition of 5 μM pa in the absence of pIND-h-Tsg101-FLAG had no inhibitory effect. Release of immature particles containing bands identified as the truncated GagΔp6 precursor protein and MA-CA was not significantly affected by Tsg101 overexpression and remained essentially unchanged (lanes 5-7). The results indicate that increased intracellular levels of Tsg101 interfered with release of wild-type Pr55$^{Gag}$ particles and that this inhibition required the presence of an intact p6 domain in Gag.

Effect of mutation of the Tsg101 SB domain. Taken together, the results above suggested that both Tsg101 deficiency and overproduction could impair mature virus particle release. However, it was also possible that the over-expressed FLAG-tagged Tsg101 protein was acting as a dominant-negative inhibitor that interfered with normal trafficking. As described above, the C-terminally located SB domain regulates the steady-state level of Tsg101 post-translationally by affecting degradation of the Tsg101 protein (Feng, G. H., Lih, C.-J., & Cohen, S. N., 2000, *Cancer Research* 60, 1736-1741), and recent evidence has implicated the 26S proteasome in this process (Li, L., Liao, J., Ruland, J., Mak, T. W., & Cohen, S. N., 2001, *Proc. Natl. Acad. Sci. USA* 98, 1619-1624). It is hypothesized that the observed reduction in viral particle release upon Tsg101 over-expression may result from adventitious degradation of Tsg101-associated Gag protein due to events associated with autoregulation. This notion predicts that over-expression of Tsg101 proteins mutated in the SB region and deficient in Tsg101 autoregulation should not lead to inhibition of virus release. The Tsg101 mutant SD5-59 protein contains a highly localized mutation in which a glycine residue replaces 4 aa (residues 348-351) in the SB domain and consequently is partially defective in its ability to down-regulate the Tag101 protein (Feng, G. H., Lih, C.-J., & Cohen, S. N., 2000, *Cancer Research* 60, 1736-1741). Western blot analysis confirmed that this protein accumulated following addition of the pa inducer or in response to transfection of increasing amounts of the mutated Tsg101-FLAG DNA (FIG. 7A).

The effect of increasing expression of SD5-59 on release of virus particles was determined by adding pa at 0, 1, and 5 μM to COS cells transfected with the mutant and rev, pol and gag or gagΔ6 and examining the culture media for virus-like particles. As expected, no virus-specific protein was released from cells expressing only rev (FIG. 7B, lane 1). The particles released from cells treated with 0 μM pa exhibited the CA composition of the mature virus particle (lane 2), consistent with the results described above (FIG. 6B, lane 2). Consistent with the hypothesis that events related to Tsg101 autoregulation interfere with virus production, expression of increasing amounts of the SD5-59 mutant protein—which is inefficient in regulation—permitted release of virus particles (lanes 3,4). Surprisingly, however, expression of the mutated Tsg101 protein also resulted in accumulation of particle-associated uncleaved Gag precursor. In contrast, particles assembled by GagΔp6 were identical to those detected when wild-type tsg101 was over-expressed (lanes 5-7). The observation that overexpression of the Tsg101 mutant resulted in release of particles containing unprocessed Gag suggests that the mutation, while allowing normal virus release, disengaged the usual coupling of virus release and Gag processing.

Figure 8A:
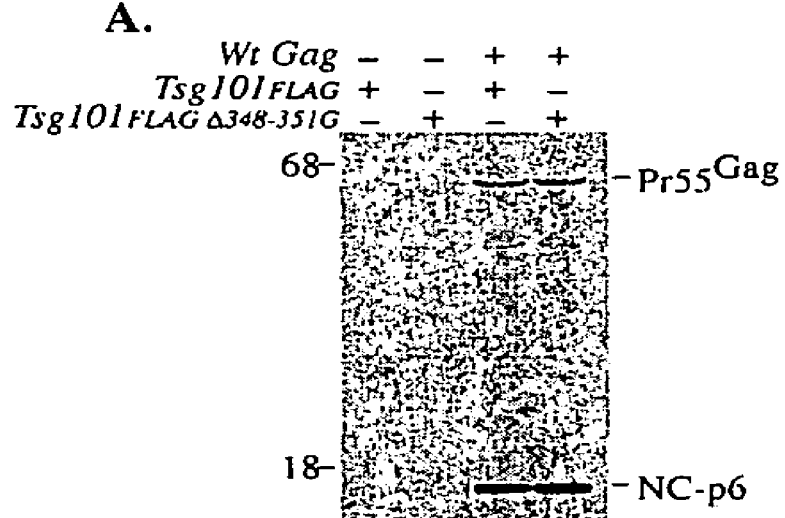
Figure 8B:
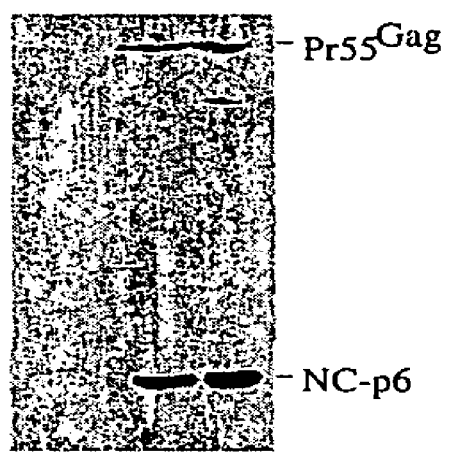
Figure 8C:
Figure 8D:
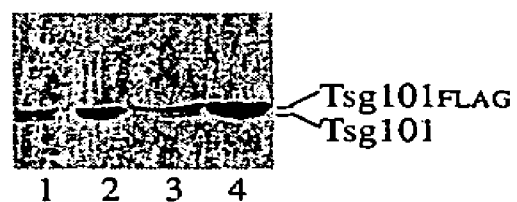

Deletion of aa348-351 is not expected to affect Tsg101 interaction with Gag because the binding site for Gag in Tsg101 resides in the N-terminal Ub E2 variant (UEV) domain. C-terminally truncated proteins lacking residues 348-351 bind Gag$^{p6}$ as efficiently as the intact protein in a 2-hybrid assay. As shown in FIG. 8, Western analysis using anti-p6 antibody indicated that the Gag$^{p6}$ precursor and the NC-p6 cleavage product accumulated in cytoplasmic extracts prepared from induced cells transfected with gag and 2 μg of either the wild-type or mutated tsg101 DNA (FIG. 8A, lanes 3,4). Anti-Tsg101 antibody immunoprecipitated the viral proteins in the 2 extracts to a comparable extent (FIG. 8B, lanes 3,4), indicating that expression of the exogenous proteins did not change the amount of Gag bound to Tsg101. Re-probing the blot with antibodies against the FLAG tag (FIG. 8C) or the full-length Tsg101 protein (FIG. 8D) confirmed the presence of the exogenous (FLAG-tagged) and native Tsg101 proteins in the immune precipitate (lanes 1-4). These results indicate that lack of effect of the SD5-59 mutation on Gag release were not due to abrogation of the Tsg101-Gag interaction.

To further test the supposition that the inhibition of virus particle release by overexpression of the wild-type Tsg101 protein results from events associated with Tsg101 autoregulation, the steady-state level of viral protein under conditions where the greatest effect on release was detected was assessed. As shown in FIG. 9A, control cells transfected with gag, pol, and rev but no exogenous tsg101 accumulated high levels of viral protein in both the S1 and P1 fractions, as revealed by Western analysis with anti-CA antibody (lanes 2, 4). In contrast, cells transfected with gag, pol, rev and wild-type tsg101-FLAG DNA under conditions that yielded the greatest inhibition (c.f. FIG. 6B, lane 4) contained no detectable viral protein in the S1 or P1 fractions, suggesting that extensive degradation of viral protein had occurred (FIG. 9B, lanes 1, 3). This effect required the p6 domain of Gag, as Gag $\Delta p^6$ was detected in both S1 and P1 fractions (lanes 2,4). Under the same conditions, cells expressing the SD5-59 mutant instead of the wild-type Tsg101 protein accumulated detectable levels of viral protein in the S1 fraction (panel C, lane 1), although no protein was found in the P1 compartment (lane 3). In contrast, Gag Δp6 accumulated at higher levels in both fractions (lanes 2,4). The results support the hypothesis that the Tsg101 autoregulatory mechanism affects the steady-state level of intracellular Gag.

Discussion

In this example, it is shown that perturbation of the steady-state level of Tsg101 by under- or over-expression of the protein negatively affected release of mature HIV-1 virus-like particles from murine and primate cells. Mutation of the Tsg101 SB region, which has been implicated in Tsg101-mediated post-translational autoregulation of its steady-state protein level reduced the ability of the over expressed Tsg101 protein to block virus particle release, as did mutation of the p6 domain. These results link the production of HIV-1 virus particles directly to a cellular protein (i.e., Tsg101) that binds the Gag L domain, which controls egress of mature virus, and provide strong evidence that the Gag-Tsg101 interaction plays a specific and significant role in HIV-1 propagation. The fact that modulation of Tsg101 expression in both murine (SL6) and primate (COS) cells affected virus release indicates that Tsg101 is an important cofactor in HIV-1 virus assembly in diverse intracellular environments.

The observation that over expression of a Tsg101 protein mutated in the SB domain resulted in release of virus particles containing Gag that was not proteolytically processed indicates that Tsg101 is involved in the Gag protein maturation associated with virus particle release. The effect of Tsg101 on release of mature virions may be a consequence of Tsg101's proposed regulation of the endocytic pathway (Lemmon, S. K. & Traub, L. M., 2000, Curr. Opin. Cell Biol. 12, 457-466). Interestingly, the mutation in SD5-59 that partially inactivates the autoregulatory mechanism lies in a region that is required for interaction with another endocytic sorting protein, Vps28 (Bishop N and Woodman P., 2001, J Biol Chem. 276:11735-42), which is included with Tsg101 in a complex that functions in trafficking of proteins between the plasma membrane and endocytic vesicles (Babst, M., Odorizzi, G., Estepa, E. J. & Emr, S. D., 2000, Traffic 1, 242-258).

Potentially, the SD5-59 mutation may have disengaged Tsg101 from the endocytic sorting machinery, causing Gag to bypass a processing site and be released in an uncleaved form. This possibility is supported by the observation that the GagΔp6 mutant, which does not bind Tsg101 and would therefore not engage the machinery, is also released in an unprocessed form.

In this regard, it is noteworthy that Tsg101-deficient SL6 cells exhibited defects in sorting and proteolytic maturation of the lysosomal hydrolase cathepsin D that are presumed to be due to failure to deliver the enzyme to the processing site in the lysosome (Babst, M., Odorizzi, G., Estepa, E. J. & Emr, S. D., 2000, Traffic 1, 242-258). The results in this example also associate Tsg101 deficiency with defective transport of Gag precursors to their normal plasma membrane maturation site. Impaired trafficking of Gag in SL6 cells may limit the pool of Gag precursors available at the membrane budding site, resulting in reduction in the amount of released particles, as we observed. As Gag lacking p6 associates with the membrane efficiently (see, e.g., Göttlinger, H. G., Dorfman, T., Sodroski, J. G. & Haseltine, W. A., 1991, Proc. Natl. Acad Sci. USA 88, 3195-3199) even though it is released less effectively (Göttlinger, H. G., Dorfman, T., Sodroski, J. G. & Haseltine, W. A., 1991, Proc. Natl. Acad Sci. USA 88, 3195-3199), transport to a specific processing site or membrane compartment, rather than membrane localization per se, may be the Gag-related event that requires normal levels of the native Tsg101 protein. Alternatively, as proteolytic processing requires the viral protease-containing Gag-Pol precursor (Swanstrom, R. & Wills, J. W., 1997, in Retroviruses, eds. Coffin, J. M., Hughes, S. H. & Varmus, H. E., Cold Spring Harbor Laboratory Press, New York, pp. 263-334), the change in efficiency of proteolytic processing mediated by the SD5-59 mutant may reflect differential effects of Tsg101 on $Gag^{p6}$ but not Gag-Pol (which lacks p6). In any ease, the fact that a mutation that may have disengaged Tsg101 from the endocytic machinery reduced the efficiency of proteolytic processing in the particles assembled in COS-1 cells links proteolytic maturation and release of HIV-1 Gag to proper functioning of proteins in the endocytic machinery. Perhaps the putative processing compartment or differential trafficking event whose existence is suggested by our results indirectly involves the proteasome, as proteasome inhibitors were found to prevent cell-mediated degradation of Tsg101 (Li, L., Liao, J., Ruland, J., Mak, T. W., & Cohen, S. N., 2001, Proc. Natl. Acad. Sci. USA 98, 1619-1624) and viral protease-mediated processing of Gag (Schubert, U., Ott, D. E., Chertova, E. N., Welker, R., Tessmer, U., Princiotta, M. F., Bennink, J. R., Krausslich, H. G. & Yewdell, J. W., 2000, Proc. Natl. Acad. Sci. USA 97, 13057-13062.).

Regarding Tsg101 control of virus release, these results suggest that the Tsg101 steady-state level and the efficiency of mature virus release are tightly coupled. Tsg101 deficiency and overproduction resulted in similar outcomes, i.e., reduced Gag accumulation in the plasma membrane-enriched S1 fraction. This example demonstrates that Tsg101 over-expression correlated with apparent degradation of Gag and that the lessened inhibitory effect of the SD5-59 mutant protein was related to reduced effects on Gag imposed by auto-regulation of Tsg101. Interestingly, under the conditions of these experiments, Gag was much more affected by over-expression of an exogenously-derived tsg101 gene than was the endogenous Tsg101 protein. This observation suggests that the form of Gag that binds Tsg101 is a multimer and that Tsg101 interaction with a subset o molecules in the multimer was sufficient to induce the observed inhibitory effects on Gag accumulation and release. This seems consistent with previous observations that efficient particle release does not require that every Gag molecule possess an L domain (Wills, J. W., Cameron, C. E., Wilson, C. B., Xiang, Y., Bennett, R. P. & Leis, J., 1994, J Virol. 68, 6605-6618), the binding site of Tsg101 in Gag as shown in Example 1. The observation also may suggest that only a subpopulation of Tsg101 molecules can form productive complexes with Gag, as the inhibition of mature virus production was aggravated by greater accumulation of the wild-type FLAG-tagged Tsg101 protein. Recent evidence indicates that Tsg101 can interact with Ub ligases Mdm2 (Li, L., Liao, J., Ruland, J., Mak, T. W., & Cohen, S. N., 2001, Proc. Natl. Acad. Sci. USA 98, 1619-1624) and Nedd4. These enzymes monoubiquitinate substrates destined for transport by the endocytic machinery (Shih, S. C., Sloper-Mould, K. E. & Hicke, L., 2000, *EMBO. J.* 19, 187-198) and polyubiquitinate cargo intended for proteasomal degradation (Hershko, A. & Ciechanover, A., 1998, *Annu. Rev. Biochem.* 67, 425-479), possibly including Tsg101 itself when it is overproduced. The notion that Tsg101 functions in concert with Ub ligases is supported by studies that implicate the Ub machinery in L domain function and viral exocytosis (Schubert, U., Ott, D. E., Chertova, E. N., Welker, R., Tessmer, U., Princiotta, M. F., Bennink, J. R., Krausslich, H. G. & Yewdell, J. W., 2000, *Proc. Natl. Acad. Sci. USA* 97, 13057-13062, Strack, B., Calistri, A., Accola, M. A., Palu, G. & Gottlinger, H. G., 2000, *Proc. Natl. Acad Sci. USA* 97, 13063-13068; Patnaik, A., Chau, V. & Wills, J. W., 2000, *Proc. Natl. Acad. Sci. USA* 97, 13069-13074; Ott, D. E., Coren, L. V., Chertova, E. N., Gagliardi, T. D. & Schubert, U., 2000, *Virology* 278, 111-121; Vogt, V. M., 2000, *Proc. Natl. Acad. Sci. USA* 97, 12945-12947). Tsg101 interaction with Ub ligases may bring these enzymes into proximity with assembling Gag particles. Gag may require tight Tsg101-mediated control to promote transport vs. degradation.

Precisely how Tsg101 might mediate trafficking of Gag is unclear. Possibly, Tsg101 controls trafficking of a membrane-associated cellular protein that regulates exocytosis. It is also noteworthy that the invagination event associated with formation of the sorting multi vesicular body (MVB) that Tsg101 is believed to regulate (Lemmon, S. K. & Traub, L. M., 2000, *Curr. Opin. Cell Biol.* 12, 457-466) is the only example in the cell, other than virus budding, where vesicle formation is directed away from the cytoplasm. Thus Gag, through its interaction with Tsg101, may become linked to other vps homologues that determine formation of the sorting MVB and may cause the machinery to direct invagination out of the cell of vesicles containing virus particles. If this strategy is indeed unique to the virus, the requirement for the interaction may provide a potential target for interfering with HIV propagation.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

```
SEQ. ID. NO. 1:
MAVSESQLKK MMSKYKYRDL TVRQTVNVIA MYDKLKPVLD SYVFNDGSSR ELVNLTGTIP   60
VRYRGNIYNI PICLWLLDTY PYNPPICFVK PTSSMTIKTG KHVDANGKIY LPYLHDWKHP  120
RSELLELIQI MIVIFGEEPP VFSRPTVSAS YPPYTATGPP NTSYMPGMPS GISAYPSGYP  180
PNPSGYPGCP YPPAGPYPAT TSSQYPSQPP VTTVGPSRDG TISEDTIRAS LISAVSDKLR  240
WRMKEEMDGA QAELNALKRT EEDLKKGHQK LEEMVTRLDQ EVAEVDKNIE LLKKKDEELS  300
SALEKMENQS ENNDIDEVII PTAPLYKQIL NLYAEENAIE DTIFYLGEAL RRGVIDLDVF  360
LKHVRLLSRK QFQLRALMQK ARKTAGLSDL Y                                391

SEQ. ID. NO. 2
MAVSESQLKK MVSKYKYRDL TVRETVNVIT LYKDLKPVLD SYVFNDGSSR ELMNLTGTIP   60
VPYRGNTYNI PICLWLLDTY PYNPPICFVK PTSSMTIKTG KHVDANGKIY LPYLHEWKHP  120
QSDLLGLIQV MIVVFGDEPP VFSRPISASY PPYQATGPPN TSYMPGMPGG ISPYPSGYPP  180
NPSGYPGCPY PPGGPYPATT SSQYPSQPPV TTVGPSRDGT ISEDTIRASL ISAVSDKLRW  240
RMKEEMDRAQ AELNALKRTE EDLKKGHQKL EEMVTRLDQE VAEVDKNIEL LKKKDEELSS  300
ALEKMENQSE NNDIDEVIIP TAPLYKQILN LYAEENAIED TIFYLGEALR RGVIDLDVFL  360
KHVRLLSRKQ FQLRALMQKA FKTAGLSDLY                                  390

SEQ. ID. NO: 3
PTAPP                                                               5

SEQ ID NO: 4
ALQSRPEPTA PPEES                                                   15
```

---

What is claimed is:

1. A method for identifying a peptide or fragment derived from a mammalian tumor susceptibility gene 101 (Tsg101) protein, wherein the peptide or fragment is effective in reducing HIV particle production, said method comprising:
   (a) introducing an expression construct into a mammalian cell or cells, wherein the expression construct comprises a portion of a mammalian tsg101 gene;
   (b) introducing one or more expression constructs into the mammalian cell or cells, wherein the one or more expression constructs comprise the HIV gag, pol, and rev gene sequences;
   (c) incubating the transfected mammalian cell or cells in a suitable media for a sufficient time and at a temperature of about 37° C. to obtain a mammalian cell culture comprising mammalian cells which express a mammalian Tsg101 peptide or fragment and HIV Gag, Pol and Rev proteins;
   (d) measuring the level of particle-associated p24 in the mammalian cell culture; and
   (e) correlating a reduced level of particle-associated p24, when compared to a control mammalian cell culture which has not been transfected with the expression construct comprising a portion of a mammalian tsg101 gene, with the identification of a peptide or fragment effective in reducing HIV particle production.

2. A method for identifying a peptide or fragment derived from a mammalian Tsg101 protein, wherein the peptide or fragment is effective in reducing HIV particle production, said method comprising:
   (a) introducing an expression construct into a mammalian cell or cells, wherein the expression construct comprises a portion of a mammalian tsg101 gene;
   (b) introducing HIV into the mammalian cell or cells;
   (c) incubating the transfected and infected mammalian cell or cells in a suitable media for a sufficient time and at a temperature of about 37° C. to obtain a mammalian cell culture comprising mammalian cells which express a mammmalian Tsg101 peptide or fragment and which produce HIV particles;
   (d) measuring the level of particle-associated p24 in the mammalian cell culture; and
   (e) correlating a reduced level of particle-associated p24, when compared to a control mammalian cell culture which has not been transfected with the expression construct comprising a portion of a mammalian tsg101 gene, with the identification of a peptide or fragment effective in reducing HIV particle production.

3. A method for identifying a peptide or fragment derived from a mammalian Tsg101 protein, wherein the peptide or fragment is effective in reducing HIV particle production, said method comprising:
   (a) introducing an expression construct into a mammalian cell or cells, wherein the expression construct comprises a portion of a mammalian tsg101 gene;
   (b) introducing HIV into the mammalian cell or cells;
   (c) incubating the transfected and infected mammalian cell or cells in a suitable media for a sufficient time and at a temperature of about 37° C. to obtain a mammalian cell culture comprising mammalian cells which express a mammalian Tsg101 peptide or fragment and which produce HIV particles;
   (d) quantifying the HIV particles released from the cells; and
   (e) correlating a reduction in HIV particle production, when compared to a control mammalian cell culture which has not been transfected with the expression construct comprising a portion of a mammalian tsg101 gene, with the identification of a peptide or fragment effective in reducing HIV particle production.

4. A method for identifying a peptide or fragment derived from a mammalian Tsg101 protein, wherein the peptide or fragment is effective in reducing HIV particle production, said method comprising:
   (a) introducing one or more expression constructs into a mammalian cell or cells, wherein the one or more expression constructs comprise the HIV gag, pol, and rev gene sequences;
   (b) introducing into the mammalian cell or cells a peptide or fragment derived from a mammalian Tsg101 protein;
   (c) incubating the mammalian cell or cells transfected with the one or more expression constructs and permeated with a peptide or fragment derived from a mammalian Tsg101 protein in a suitable media for a sufficient time and at a temperature of about 37° C. to obtain a cell culture;
   (d) measuring the level of particle-associated p24 in the mammalian cell culture; and
   (e) correlating a reduced level of particle-associated p24, when compared to a control mammalian cell culture which has not been permeated with a peptide or fragment derived from a mammalian Tsg101 protein, with the identification of a peptide or fragment effective in reducing HIV particle production.

5. A method for identifying a peptide or fragment derived from a mammalian Tsg101 protein, wherein the peptide or fragment is effective in reducing HIV particle production, said method comprising:
   (a) introducing HIV into a mammalian cell or cells;
   (b) introducing into the mammalian cell or cells a peptide or fragment derived from a mammalian Tsg101 protein;
   (c) incubating the mammalian cell or cells transfected with HIV and permeated with a peptide or fragment derived from a mammalian Tsg101 protein in a suitable media for a sufficient time and at a temperature of about 37° C. to obtain a cell culture;
   (d) measuring the level of particle-associated p24 in the cell culture; and
   (e) correlating a reduced level of particle-associated p24, when compared to a control mammalian cell culture which has not been permeated with a peptide or fragment derived from a mammalian Tsg101 protein, with the identification of a peptide or fragment effective in reducing HIV particle production.

6. A method for identifying a peptide or fragment derived from a mammalian Tsg101 protein, wherein the peptide or fragment is effective in reducing HIV particle production, said method comprising:
- (a) introducing HIV into a mammalian cell or cells;
- (b) introducing into the mammalian cell or cells a peptide or fragment derived from a mammalian Tsg101 protein;
- (c) incubating the mammalian cell or cells transfected with HIV and permeated with a peptide or fragment derived from a mammalian Tsg101 protein in a suitable media and for a sufficient time at a temperature of about 37° C.;
- (d) quantifying the HIV particles released from the cells; and
- (e) correlating a reduction in HIV particle production, when compared to a control mammalian cell culture which has not been permeated with a peptide or fragment derived from a mammalian Tsg101 protein, which the identification of a peptide or fragment effective in reducing HIV particle production.

7. The method of any one of claims 1, 2 or 3, wherein the coding sequence for a mammalian tsg101 gene is the coding sequence for the ubiquitin E2 variant (UEV) A domain of Tsg101 protein.

8. A method for identifying a peptide or fragment derived from a mammalian Tsg101 protein, wherein said peptide or fragment is effective in reducing HIV particle production, said method comprising:
- (a) measuring a level of HIV particles released in a culture of mammalian cells, wherein said mammalian cells comprise an expression construct comprising a portion of a mammalian tsg101 gene such that said mammalian cells express a mammalian Tsg101 peptide or fragment and are infected by HIV virus; and
- (b) comparing said level of HIV particles to a level of HIV particles released in a culture of control mammalian cells under similar conditions, wherein said control mammalian cells do not comprise an expression construct comprising a portion of a mammalian tsg101 gene and are infected by HIV virus, wherein said level of HIV particles measured in step (a) compared to said level of HIV particles of said culture of control mammalian cells below a predetermined threshold level identify said mammalian Tsg101 peptide or fragment as effective in reducing HIV particle production.

9. A method for identifying a peptide or fragment derived from a mammalian Tsg101 protein, wherein said peptide or fragment is effective in reducing HIV particle production, said method comprising:
- (a) measuring a level of HIV viral particle released in a culture of mammalian cells, wherein said mammalian cells comprise (i) an expression construct comprising a portion of a mammalian tsg101 gene and (ii) an expression construct comprising the HIV gag, pol and rev gene sequence, such that said mammalian cells express a mammalian Tsg101 peptide or fragment and HIV Gag, Pol and Rev proteins; and
- (b) comparing said level of HIV particles released to a level of HIV particles released in a culture of control mammalian cells under similar conditions, wherein said control mammalian cells comprise one or more expression constructs comprising the HIV gag, pol and rev gene sequences such that said mammmalian cells express HIV Gag, Pol and Rev protein and wherein said control mammalian cells do not comprise an expression construct comprising a portion of a mammalian tsg101 gene, wherein said level of HIV particles measured in step (a) compared to said level of HIV particles released in said culture of control mammalian cells below a predetermined thershold level identify said mammalian Tsg101 peptide or fragment as effective in reducing HIV particle production.

10. A method for identifying a peptide or fragment derived from a mammalian Tsg101 protein, wherein said peptide or fragment is effective in reducing HIV particle production, said method comprising:
- (a) measuring a level of HIV viral particle released in a culture of mammalian cells, wherein said mammalian cells comprise (i) an expression construct comprising a portion of a mammalian tsg101 gene and (ii) an expression construct comprising the HIV gag gene sequence, such that said mammalian cells express a mammalian Tsg101 peptide or fragment and HIV Gag protein; and
- (b) comparing said level of HIV viral particle released to a level of HIV viral particle released in a culture of control mammalian cells under similar conditions, wherein said control mammalian cells comprise one or more expression constructs comprising said HIV gag gene sequence such that said mammalian cells express HIV Gag and wherein said control mammalian cells do not comprise an expression construct comprising a portion of a mammalian tsg101 gene, wherein said level of HIV viral particle measured in step (a) compared to said level of HIV viral particle released in said culture of control mammalian cells below a predetermined threshold level identify said mammalian Tsg101 peptide or fragment as effective in reducing HIV particle production.

11. The method of claim 8, 9, or 10, wherein said level of HIV particles released in a culture of mammalian cells and said level of HIV particles released in a culture of control mammalian cells are represented by measured levels of particle-associated p24.

12. The method of claim 8, 9, or 10, wherein said portion of mammalian tsg101 gene is a coding sequence for the UEV A domain of said Tsg101 protein.

13. The method of claim 12, wherein said predetermined threshold level is a two-fold reduction of said level of HIV particles measured in step (a) compared to said level of HIV particles of said culture of control mammalian cells.

14. The method of claim 12, wherein said predetermined threshold level is a four-fold reduction of said level of HIV particles measured in step (a) compared to said level of HIV particles of said culture of control mammalian cells.

15. The method of claim 14, wherein said predetermined threshold level is a 90% reduction of said level of HIV particles measured in step (a) compared to said level of HIV particles of said culture of control mammalian cells.

16. The method of claim 15, wherein said predetermined threshold level is a 95% reduction of said level of HIV particles measured in step (a) compared to said level of HIV particles of said culture of control mammalian cells.

17. The method of claim 16, wherein said predetermined threshold level is a 99% reduction of said level of HIV particles measured in step (a) compared to said level of HIV particles of said culture of control mammalian cells.

18. The method of claim 17, wherein said predetermined threshold level is a 99.5% reduction of said level of HIV particles measured in step (a) compared to said level of HIV particles of said culture of control mammalian cells.

19. A method for identifying a peptide or fragment derived from a mammalian Tsg101 protein, wherein said peptide or fragment is effective in reducing retrovirus production, said method comprising identifying a peptide that binds to a peptide comprising the PTAP (SEQ ID NO: 39) motif of a retroviral protein.

20. The method of claim 19, wherein said retrovirus is a lentivirus.

21. The method of claim 20, wherein said lentivirus is HIV-1 virus.

22. The method of claim 20, wherein said lentivirus is HIV-2 virus.

23. The method of claim 20, wherein said lentivirus is simian immunodeficiency virus.

24. The method of claim 19, wherein said peptide comprising the PTAP (SEQ ID NO: 39) motif is a HIV Gag protein.

25. The method of claim 19, wherein said peptide comprising the PTAP (SEQ ID NO: 39) motif is the peptide of SEQ ID NO:4.

26. The method of any one of claims 8-10, wherein said tsg101 gene is a human tsg101 gene.

* * * * *